United States Patent
Tanabe et al.

(10) Patent No.: US 9,645,117 B2
(45) Date of Patent: May 9, 2017

(54) PIEZOELECTRIC UNIT, PIEZOELECTRIC DEVICE, PIEZOELECTRIC DETERMINATION APPARATUS, AND STATE DETERMINATION METHOD

(71) Applicant: SEIKO INSTRUMENTS INC., Chiba-shi, Chiba (JP)

(72) Inventors: Sachiko Tanabe, Chiba (JP); Masayuki Suda, Chiba (JP); Hiroshi Muramatsu, Chiba (JP)

(73) Assignee: SEIKO INSTRUMENTS INC. (JP)

( * ) Notice: Subject to any disclaimer, the term of this patent is extended or adjusted under 35 U.S.C. 154(b) by 109 days.

(21) Appl. No.: 14/409,265

(22) PCT Filed: May 21, 2013

(86) PCT No.: PCT/JP2013/064110
§ 371 (c)(1),
(2) Date: Dec. 18, 2014

(87) PCT Pub. No.: WO2014/002650
PCT Pub. Date: Jan. 3, 2014

(65) Prior Publication Data
US 2015/0198562 A1    Jul. 16, 2015

(30) Foreign Application Priority Data
Jun. 25, 2012  (JP) ................ 2012-141743

(51) Int. Cl.
*G01N 29/02*  (2006.01)
*G01N 11/16*  (2006.01)
(Continued)

(52) U.S. Cl.
CPC ........... *G01N 29/022* (2013.01); *G01N 11/16* (2013.01); *G01N 29/028* (2013.01);
(Continued)

(58) Field of Classification Search
CPC ............... G01N 29/022; G01N 11/16; G01N 2291/022; G01N 2291/0422; G01N 5/02;
(Continued)

(56) References Cited

U.S. PATENT DOCUMENTS 3,879,992 A * 4/1975 Bartera ................. G01B 7/066
                                                      310/312
3,992,760 A * 11/1976 Roberts ................ G01R 29/22
                                                      29/25.35
(Continued)

OTHER PUBLICATIONS

International Search Report mailed Jul. 2, 2013 issued in International Appln. No. PCT/JP2013/064110.

*Primary Examiner* — Hezron E Williams
*Assistant Examiner* — Marrit Eyassu
(74) *Attorney, Agent, or Firm* — Adams & Wilks

(57) ABSTRACT

A piezoelectric unit 1 includes a piezoelectric element that causes thickness shear vibration, a first electrode provided on one surface of the piezoelectric element, a second electrode and a third electrode which are provided on an opposite surface to the one surface which is provided with the first electrode of the piezoelectric element and are electrically insulated from each other, and a switching portion that is connected to the first electrode, the second electrode, and the third electrode, in which the switching portion can switch measurement modes between a mass/viscoelasticity measurement mode for measuring mass of a substance which is in contact with the piezoelectric element or viscoelasticity by vibrating the piezoelectric element, and an electrical characteristic measurement mode for measuring electrical characteristics between the second electrode and the third electrode.

29 Claims, 18 Drawing Sheets

(51) Int. Cl.
  *G01N 29/028* (2006.01)
  *H01L 41/047* (2006.01)
  *H03H 9/15* (2006.01)
  *H03H 9/25* (2006.01)
  *H03H 9/17* (2006.01)
  *G01N 5/02* (2006.01)
  *G01N 9/34* (2006.01)

(52) U.S. Cl.
  CPC .............. *H01L 41/047* (2013.01); *H03H 9/15* (2013.01); *H03H 9/177* (2013.01); *H03H 9/25* (2013.01); *G01N 5/02* (2013.01); *G01N 9/34* (2013.01); *G01N 2291/022* (2013.01); *G01N 2291/0256* (2013.01); *G01N 2291/02818* (2013.01); *G01N 2291/0422* (2013.01); *G01N 2291/0426* (2013.01)

(58) Field of Classification Search
  CPC .................... G01N 9/34; G01N 29/028; G01N 2291/0256; G01N 2291/02818; G01N 2291/0426; H03H 9/15; H03H 9/25; H03H 9/177; H01L 41/047
  USPC .............................................. 73/54.41, 24.01
  See application file for complete search history.

(56) References Cited

U.S. PATENT DOCUMENTS

| | | | | |
|---|---|---|---|---|
| 6,111,342 | A * | 8/2000 | Muramatsu | G01N 29/036 310/311 |
| 2009/0165560 | A1* | 7/2009 | Lee | G01G 3/13 73/580 |
| 2009/0288488 | A1* | 11/2009 | Yamakawa | H01L 41/1132 73/579 |
| 2012/0219458 | A1* | 8/2012 | Kukita | G01N 29/022 422/69 |

* cited by examiner (STATE A)

(STATE B)

(STATE A)

(STATE B)

(STATE A2)

(STATE B2)

(STATE A3)

(STATE B3)

PIEZOELECTRIC UNIT, PIEZOELECTRIC DEVICE, PIEZOELECTRIC DETERMINATION APPARATUS, AND STATE DETERMINATION METHOD

BACKGROUND OF THE INVENTION

TECHNICAL FIELD

The present invention relates to a piezoelectric unit, a piezoelectric device, a piezoelectric determination apparatus, and a state determination method capable of measuring physical properties by using thickness shear vibration of a piezoelectric element.

BACKGROUND ART

As for a method of measuring physical properties using a quartz crystal vibrator which causes thickness shear vibration, a quartz crystal vibrator microbalance (QCM) measurement method is known (for example, refer to PTL 1). The QCM measurement method is, for example, a method of measuring a concentration of a specific substance by adding an organic polymer film which selectively adsorbs the specific substance in addition to a structure of a general quartz crystal vibrator in which a single electrode is provided on each of both sides of a quartz crystal plate. As mentioned above, there are various characteristics which can be measured by using the QCM measurement method. However, characteristics which can be measured by using a QCM sensor are typically limited to a single characteristic.

Meanwhile, there is a case where, depending on a measurement target, a single characteristic is not sufficient, and a measurement is not meaningful unless two or more characteristics are acquired simultaneously. For example, in a case where the viscosity of a liquid is examined, the viscosity depends on a temperature, and thus the temperature is required to be simultaneously measured at the same measurement point as the viscosity. Therefore, in a case where the QCM sensor of the related art is used, it is necessary to prepare a temperature sensor along with the QCM sensor for measuring viscosity.

In addition, in a case where viscosity and a temperature are measured by using the QCM sensor of the related art and the temperature sensor, if measurement points of the viscosity and temperature are spaced apart from each other, there is a problem in that a temperature difference occurs between both measurement points when a temperature of a liquid rapidly varies or fluctuates, and thus a combination of incorrect measured values of the temperature and viscosity may be obtained.

For this reason, there is demand for an integrated sensor in which a QCM sensor and another sensor are integrally formed.

Therefore, as an example of such an integrated sensor, a sensor has been proposed in which a separate temperature sensor or a capacitance type sensor is added to a surface or a lower part of a quartz crystal vibrator in addition to a general structure of the quartz crystal vibrator (for example, refer to PTL 2).

CITATION LIST

Patent Literature

[PTL 1] JP-A-2010-71716
[PTL 2] JP-T-2006-522918

Meanwhile, the QCM sensor is a sensor which acquires physical property information of a medium by measuring a resonance frequency or an equivalent circuit constant of a quartz crystal vibrator since a vibration characteristic of the quartz crystal vibrator at the time of causing thickness shear vibration reflects a state of the medium which is in contact with a quartz crystal plate. Therefore, as disclosed in the related art, in a case where a structure is employed in which a separate sensor is provided on a surface, an outer circumference, or the like of the quartz crystal plate, there is a probability that stress occurring due to the provision of the separate sensor may influence thickness shear vibration, and thus a measurement using the QCM sensor may not be accurately performed.

Accordingly, the present invention has been made in light of these circumstances, and an object thereof is to provide a piezoelectric unit, a piezoelectric device, a piezoelectric determination apparatus, and a state determination method in which two or more physical properties of a measurement target are acquired simultaneously and thickness shear vibration is hardly influenced.

SUMMARY OF THE INVENTION

In order to achieve the above object, the present invention provides the following means.

In a first feature of a piezoelectric unit related to the present invention, the piezoelectric unit includes a piezoelectric element that causes thickness shear vibration; an electrode portion that includes a first electrode provided on one surface of the piezoelectric element, and a second electrode and a third electrode which are provided on an opposite surface to the one surface of the piezoelectric element and are electrically insulated from each other; and a switching portion that is connected to the first electrode, the second electrode, and the third electrode, and switches a connection state of each electrode, in which the switching portion can switch a measurement mode between a mass/viscoelasticity measurement mode which is a connection state of the electrodes for measuring mass or viscoelasticity of a substance which is in contact with the piezoelectric element by causing the thickness shear vibration of the piezoelectric element, and an electrical characteristic measurement mode which is a connection state of the electrodes for measuring electrical characteristics between the second electrode and the third electrode.

According to the feature of the related piezoelectric unit, the piezoelectric unit has a structure in which at least one of the second electrode and the third electrode has two functions including a function of a single electrode and a function of a pair of electrodes formed by the second electrode and the third electrode as electrodes applying a signal to the piezoelectric element. Therefore, when the piezoelectric unit is used to measure a physical property, it is possible to acquire at least two pieces of physical property information without providing other measurement devices on the piezoelectric element through a measurement using thickness shear vibration and a measurement using a pair of electrodes formed by the second electrode and the third electrode. Therefore, it is possible to implement a composite sensor which hardly influences thickness shear vibration.

In a second feature of the piezoelectric unit related to the present invention, the piezoelectric element is a quartz crystal vibrator.

According to the feature of the related piezoelectric unit, it is possible to implement a composite sensor with high measurement stability, using thickness shear vibration, by using a quartz crystal vibrator which allows stable thickness shear vibration to be obtained as the piezoelectric element.

In a third feature of the piezoelectric unit related to the present invention, the second electrode and the third electrode have a comb shape.

According to the feature of the related piezoelectric unit, the second electrode and the third electrode have a comb shape, and thus a path through which a signal flows via a measurement target object can be increased, thereby performing a measurement with high sensitivity, in a case where the second electrode and the third electrode are formed by a pair of electrodes and are used to measure physical properties (when the switching portion is in the second state).

In a fourth feature of the piezoelectric unit related to the present invention, the mass/viscoelasticity measurement mode is a connection state in which the second electrode and the third electrode are maintained at an equal potential so that a pseudo integrated electrode is formed, and a potential difference is formed between the integrated electrode and the first electrode.

According to the feature of the related piezoelectric unit, area ratios of the electrodes on the front and rear surfaces of the piezoelectric element can be closer to each other, and thus the piezoelectric element can be made to stably vibrate, thereby performing a measurement with high sensitivity.

In a fifth feature of the piezoelectric unit related to the present invention, the mass/viscoelasticity measurement mode is a connection state in which a potential difference is formed between the first electrode and one of the second electrode and the third electrode.

According to the feature of the related piezoelectric unit, switching performed by the switching portion can be further simplified, and thus it is possible to more easily configure the piezoelectric unit which acquires two or more physical properties.

In a sixth feature of the piezoelectric unit related to the present invention, the electrical characteristic measurement mode is a connection state in which a potential difference is formed between the second electrode and the third electrode in a state in which the first electrode is short-circuited to one of the second electrode and the third electrode.

According to the feature of the related piezoelectric unit, the first electrode is connected to either the second electrode or the third electrode, and thus it is possible to remove regulation capacitance of a measurement system, thereby performing a measurement, especially, in a high frequency region with high accuracy.

In a seventh feature of the piezoelectric unit related to the present invention, a region surrounded by an exterior of the first electrode has the same area as an area of a region surrounded by a combined exterior of the second electrode and the third electrode, and relative positions of the electrodes on front and rear surfaces with the piezoelectric element interposed therebetween match each other.

According to the feature of the related piezoelectric unit, it is possible to make the piezoelectric element more stably vibrate, and thus to perform a measurement with high sensitivity.

In an eighth feature of the piezoelectric unit related to the present invention, the piezoelectric element is provided with a sensitive film on the front surface.

According to the feature of the related piezoelectric unit, in a case where the piezoelectric element is provided with the sensitive film to which a specific substance is attached, it is possible to easily measure concentration, density, an amount of insoluble particles, mass, or the like of a specific substance included in a liquid or a gas when a measurement using thickness shear vibration is performed. In addition, in a case where the piezoelectric element is provided with a sensitive film whose viscoelasticity greatly varies due to coupling with a minute amount of substances, it is possible to improve measurement sensitivity in a measurement using thickness shear vibration.

In a first feature of a piezoelectric device related to the present invention, the piezoelectric device includes the piezoelectric unit having any one of the first to eighth features; a first circuit unit that is connected to the piezoelectric unit; and a second circuit unit that is connected to the piezoelectric unit, in which the first circuit unit includes a first signal applying circuit that applies a first input signal to the electrode portion in a connection state of the mass/viscoelasticity measurement mode, and in which the second circuit unit includes a second signal applying circuit that applies a second input signal to the electrode portion in a connection state of the electrical characteristic measurement mode.

According to the feature of the related piezoelectric device, the piezoelectric device is formed by using the piezoelectric unit which has a structure in which both of the second electrode and the third electrode have two functions including a function of a single electrode and a function of a pair of electrodes formed by the second electrode and the third electrode as electrodes applying a signal to the piezoelectric element. Therefore, when the piezoelectric device is used to measure a physical property, it is possible to implement a composite sensor which hardly influences thickness shear vibration.

In a second feature of the piezoelectric device related to the present invention, the first circuit unit includes a first signal detection circuit that detects a first output signal responding to the first input signal, and can measure a first physical quantity based on the first output signal, and the second circuit unit includes a second signal detection circuit that detects a second output signal responding to the second input signal which is applied by the second signal applying circuit, and can measure a second physical quantity based on the second output signal.

According to the feature of the related piezoelectric device, in the first state, the first input signal, which is applied between the integrated electrode and the first electrode by the first signal applying circuit included in the first circuit unit, causes thickness shear vibration reflecting a physical property of a substance which is in contact with the piezoelectric element in the piezoelectric element of the piezoelectric unit, and the first signal detection circuit measures a thickness shear vibration state so as to measure the first physical quantity of the substance.

In addition, in the second state, the second signal applying circuit included in the second circuit unit causes the second electrode and the third electrode to input the second input signal to a substance interposed therebetween, and the second signal detection circuit measures an electrical signal which has passed through the substrate so as to measure the second physical quantity of the substance.

Further, in the first circuit unit and the second circuit unit of the related piezoelectric device, if the signal detection circuit and the signal applying circuit are integrally formed, it becomes easier to control phases of signals or detect a phase difference thereof in both the inputting and outputting of the signals, and thus it is possible to implement a more accurate measurement device.

In a third feature of the piezoelectric device related to the present invention, the first signal applying circuit includes an oscillator circuit that can set any frequency of an applied signal.

According to the feature of the related piezoelectric unit, the first signal applying circuit includes the oscillator circuit, and thus it is possible to set any frequency of an AC voltage applied to the piezoelectric element. Therefore, it is possible to easily obtain equivalent circuit constants of the piezoelectric element.

In a fourth feature of the piezoelectric device related to the present invention, a frequency $f_{II}$ of an input signal which is input by the second signal applying circuit in a state in which the piezoelectric element is in contact with a substance having the first physical quantity or the second physical quantity satisfies (Expression 1) which is a conditional expression using a resonance frequency f which is acquired on the basis of the first output signal detected by the first signal detection circuit in a state of being in contact with the substance.

[Expression 1]

$$(f_{II} > 1.05 \times nf) \cap (f_{II} < 0.95 \times nf), n=1,3,5,\quad\text{(Expression 1)}$$

According to the feature of the related piezoelectric device, since a frequency applied between the second electrode and the third electrode excludes a resonance frequency of the piezoelectric element and a frequency band of overtone vibration, it is possible to reduce noise in a measured value of the second physical quantity and thus to perform a measurement with higher accuracy.

In a fifth feature of the piezoelectric device related to the present invention, the first signal applying circuit is an oscillation circuit which causes oscillation at a resonance frequency in a fundamental mode or harmonic vibration of the piezoelectric element.

According to the feature of the related piezoelectric device, an oscillation circuit is used as the first signal applying circuit, and thus it is possible to make the piezoelectric element easily vibrate.

In a sixth feature of the piezoelectric device related to the present invention, the second signal applying circuit includes an oscillator circuit that can set any frequency of an applied signal.

According to the feature of the related piezoelectric device, the second signal applying circuit includes the oscillator circuit, and thus it is possible to set any frequency of an AC voltage applied between the second electrode and the third electrode. Therefore, it is possible to easily obtain electrical characteristics or electrochemical characteristics of a substance interposed between the second electrode and the third electrode. In addition, it is possible to measure various characteristics.

In a seventh feature of the piezoelectric device related to the present invention, the first circuit unit and the second circuit unit are formed by an identical common unit.

According to the feature of the related piezoelectric device, the first circuit unit and the second circuit unit are made common, and thus the piezoelectric device can be miniaturized.

In an eighth feature of the piezoelectric device related to the present invention, the first signal applying circuit and the second signal applying circuit are formed by an identical common signal applying circuit, and the common signal applying circuit includes an oscillator circuit that can set any frequency.

According to the feature of the related piezoelectric device, the signal applying circuits are made common, and thus it is possible to simplify a configuration of the piezoelectric device.

In a ninth feature of the piezoelectric device related to the present invention, the first signal detection circuit and the second signal detection circuit are formed by an identical common signal detection circuit.

According to the feature of the related piezoelectric device, the signal detection circuits are made common, and thus it is possible to simplify a configuration of the piezoelectric device.

In a tenth aspect of the piezoelectric device related to the present invention, the first signal detection circuit acquires, as a first output value, any one of admittance, conductance, susceptance, inductance, reactance, resistance, impedance, capacitance, and a resonance frequency during shear vibration of the piezoelectric element on the basis of the detected first output signal.

According to the feature of the related piezoelectric device, as the first output value, at least one of admittance, conductance, susceptance, inductance, reactance, resistance, impedance, capacitance, and a resonance frequency during thickness shear vibration of the piezoelectric element is acquired, and thus the piezoelectric device can be used to measure a physical quantity of a liquid or a gas.

In an eleventh feature of the piezoelectric device related to the present invention, the first physical quantity is at least one of viscosity, elasticity, viscoelasticity, concentration, density, an amount of insoluble particles, a temperature, and mass based on the first output value.

According to the feature of the related piezoelectric device, the piezoelectric device can be used as a device which measures at least one of physical quantities such as viscosity, elasticity, viscoelasticity, concentration, density, an amount of insoluble particles, a temperature, and mass of a liquid or a gas, or a measurement device or a determination device using such physical quantities.

In a twelfth feature of the piezoelectric device related to the present invention, the second signal detection circuit acquires, as a second output value, any one of current, a potential difference, impedance, admittance, conductance, susceptance, inductance, reactance, resistance, and capacitance on the basis of the detected second output signal.

According to the feature of the related piezoelectric device, as the second output value, at least one of a potential difference, current, impedance, admittance, conductance, susceptance, inductance, reactance, resistance, and capacitance is acquired by using a pair of electrodes formed by the second electrode and the third electrode, and thus the piezoelectric device can be used to measure a physical quantity of a liquid or a gas interposed between the second electrode and the third electrode.

In a thirteenth feature of the piezoelectric device related to the present invention, the second physical quantity is at least one of electric conductivity, ionic conductivity, a dielectric constant, ion concentration, an oxidation-reduction potential, and oxidation-reduction substance concentration based on the second output value.

According to the feature of the related piezoelectric device, the piezoelectric device can be used as a device which measures at least one of physical quantities such as electric conductivity, ionic conductivity, a dielectric constant, ion concentration, an oxidation-reduction potential, and oxidation-reduction substance concentration of a liquid or a gas, or a measurement device or a determination device using such physical quantities.

In a first feature of a piezoelectric determination apparatus related to the present invention, the piezoelectric determination apparatus includes the piezoelectric device having any one of the second to thirteenth features; and a determination device that is connected to the first signal detection circuit and the second signal detection circuit, in which the determination device determines a state of a substance by using the first physical quantity and the second physical quantity.

According to the feature of the related piezoelectric determination apparatus, the piezoelectric determination apparatus is formed by using the piezoelectric unit which has a structure in which both of the second electrode and the third electrode have two functions including a function of a single electrode and a function of a pair of electrodes formed by the second electrode and the third electrode as electrodes applying a signal to the piezoelectric element. Therefore, it is possible to implement the determination apparatus by using a composite sensor which hardly influences thickness shear vibration.

In a second feature of the piezoelectric determination apparatus related to the present invention, the determination device includes a display portion that displays a result of determination performed by the determination device.

According to the feature of the related piezoelectric determination apparatus, the determination device includes the display portion, and thus it is possible to easily confirm a determination result.

In a third feature of the piezoelectric determination apparatus related to the present invention, the determination device further includes a temperature management portion that measures a temperature of the substance.

According to the feature of the related piezoelectric determination apparatus, a physical quantity is measured while measuring a temperature, and thus it is possible to more accurately determine a state of a substance.

In a fourth feature of the piezoelectric determination apparatus related to the present invention, the temperature management portion includes a temperature control section that controls a temperature of the substance.

According to the feature of the related piezoelectric determination apparatus, it is possible to determine a state of a substance under the same temperature condition by measuring a physical quantity while controlling a temperature. Thus, it is possible to perform determination of a state more accurately even if a substrate or a piezoelectric element which is highly dependent on a temperature is used.

In a first feature of a state determination method related to the present invention, the method is of determining a state of a substance by using the piezoelectric determination apparatus having the first or second feature, and the method includes measuring the first physical quantity and the second physical quantity; and determining a state of the substance by using both the first physical quantity and the second physical quantity.

According to the feature of the related characteristic state determination method, characteristics or states of a substance are determined by using the piezoelectric unit which has a structure in which at least one of the second electrode and the third electrode has two functions including a function of a single electrode and a function of a pair of electrodes formed by the second electrode and the third electrode as electrodes applying a signal to the piezoelectric element. As a result, it is possible to determine characteristics, states, or the like of a substance on the basis of two or more characteristics of the substance, and thus to derive a determination result with higher reliability.

In a second feature of the state determination method related to the present invention, the substance is a liquid, and the state is a deterioration state of characteristics of the liquid.

According to the feature of the related state determination method, a deterioration state of the liquid is determined by using the piezoelectric unit which has a structure in which at least one of the second electrode and the third electrode has two functions including a function of a single electrode and a function of a pair of electrodes formed by the second electrode and the third electrode as electrodes applying a signal to the piezoelectric element, and thus the deterioration state of the liquid can be determined on the basis of two or more characteristics of the liquid. Therefore, it is possible to perform determination of deterioration of a liquid with higher reliability.

According to the present invention, it is possible to provide a piezoelectric unit, a piezoelectric device, a piezoelectric determination apparatus, and a state determination method in which two or more physical properties of a measurement target are acquired and thickness shear vibration is hardly influenced.

DETAILED DESCRIPTION OF THE EMBODIMENTS

[First Embodiment]

Hereinafter, with reference to FIGS. 1 to 5, a description will be made of a first embodiment of a piezoelectric device and a measurement method performed by the piezoelectric device according to the present invention.

Figure 1:
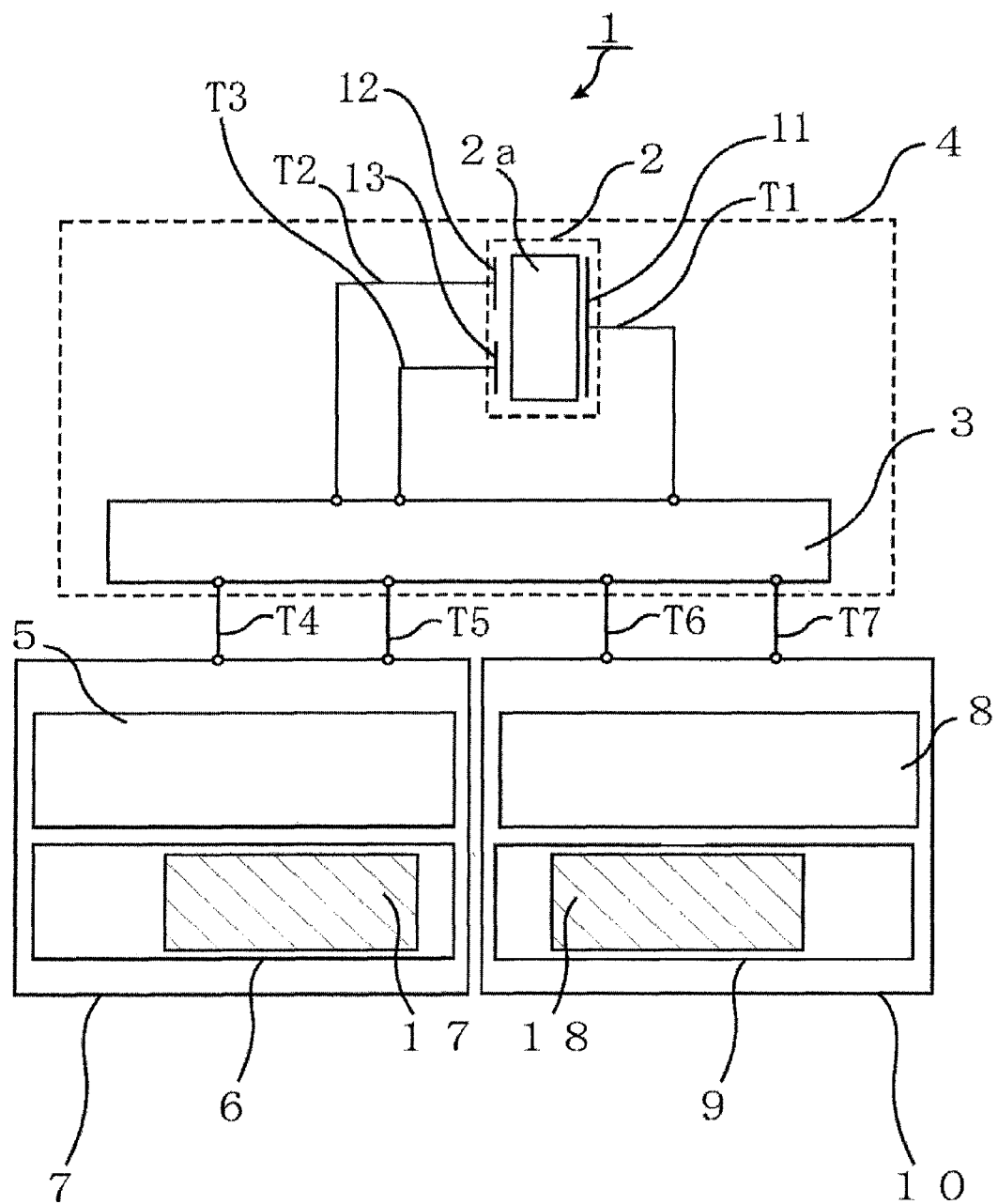
FIG. 1 is a configuration diagram illustrating a first embodiment of a piezoelectric device according to the present invention.

FIG. 1 is a configuration diagram illustrating the first embodiment of a piezoelectric device 1 according to the present invention. The piezoelectric device 1 includes a piezoelectric unit 4, a first circuit unit 7, and a second circuit unit 10.

The piezoelectric unit 4 includes a piezoelectric vibrator 2 which is a piezoelectric element, and a switching portion 3 connected to the piezoelectric vibrator 2 via connection portions T1, T2 and T3. The piezoelectric vibrator 2 is constituted by a first electrode 11 to a third electrode 13, and a piezoelectric plate 2a of which the first electrode 11 is provided on a front surface, and the second electrode 12 and the third electrode 13 are provided on a rear surface in a state of being electrically insulated from each other. In addition, a portion including the first electrode 11 to the third electrode 13 is referred to as an electrode portion for convenience. The switching portion 3 has a function of arbitrarily switching a connection state of each electrode on the piezoelectric vibrator 2 and the circuit units. Further, detailed configurations of the piezoelectric vibrator 2 and the switching portion 3 will be described later.

The first circuit unit 7 is constituted by a first signal detection circuit 5 and a first signal applying circuit 6, and is connected to the piezoelectric unit 4 (switching portion 3) via connection portions T4 and T5. In addition, the second circuit unit 10 is constituted by a second signal detection circuit 8 and a second signal applying circuit 9, and is connected to the piezoelectric unit 4 (switching portion 3) via connection portions T6 and T7. Here, the first signal applying circuit 6 and the second signal applying circuit 9 respectively include oscillator circuits 17 and 18, and thus can apply a voltage of any frequency or any amplitude between the connection portion T4 and the connection portion T5 or between the connection portion T6 and the connection portion T7. In other words, the first signal applying circuit 6 and the second signal applying circuit 9 include the oscillator circuits 17 and 18 and thus can set any frequency of a signal applied to the piezoelectric element. In addition, the first signal detection circuit 5 and the second signal detection circuit 8 detect an output signal based on a potential difference which is formed between the electrodes.

(Configuration of Piezoelectric Vibrator)

Next, a detailed configuration of the piezoelectric vibrator 2 will be described.

Figure 2A:
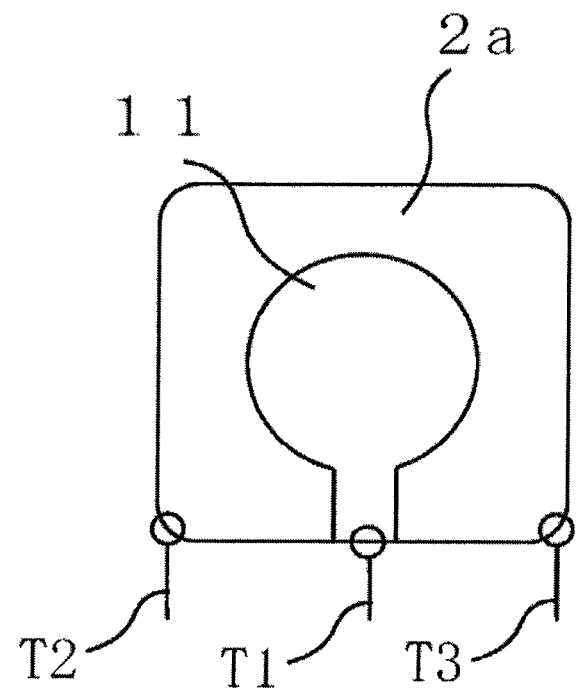
FIGS. 2(a) and 2(b) are schematic diagrams respectively illustrating (a) a front surface and (b) a rear surface of a piezoelectric plate of the first embodiment.
Figure 2B:
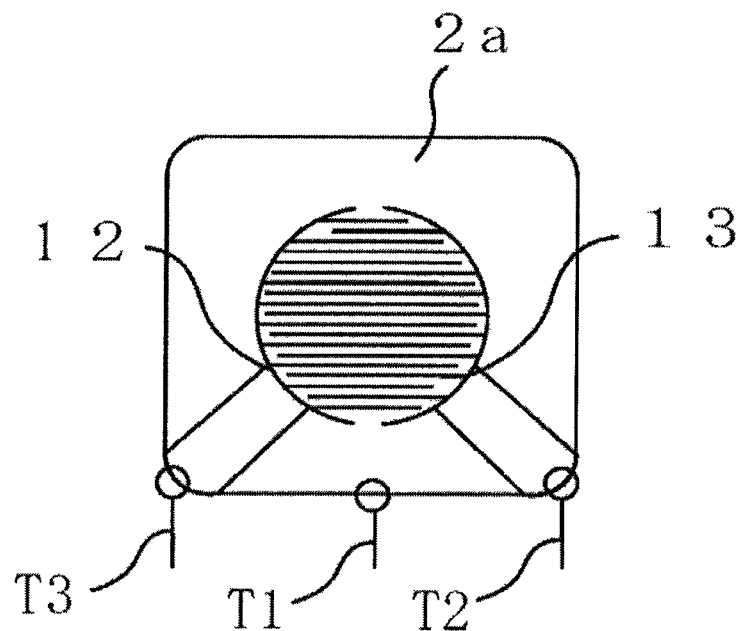

FIGS. 2(a) and 2(b) are schematic diagrams respectively illustrating a front surface and a rear surface of the piezoelectric plate 2a. The piezoelectric plate 2a of the piezoelectric vibrator 2 is cut so as to cause thickness shear vibration, and, particularly, is preferably an AT cut quartz crystal. In other words, the piezoelectric device 1 can implement a composite sensor with high measurement stability, using thickness shear vibration, by using a quartz crystal vibrator as the piezoelectric element.

As illustrated in FIG. 2 (a), the first electrode 11 which is a solid electrode is provided on the front surface of the piezoelectric plate 2a. In addition, the first electrode 11 is connected to the switching portion 3 via the connection portion T1. On the other hand, as illustrated in FIG. 2 (b), the second electrode 12 and the third electrode 13 are provided on the rear surface of the piezoelectric plate 2a in a state of being electrically insulated from each other. In addition, the second electrode 12 and the third electrode 13 are formed by a pair of comb-shaped electrodes. As mentioned above, the second electrode 12 and the third electrode 13 have a comb shape, and thus a path through which a signal flows via a measurement target object can be increased, thereby performing a measurement with high sensitivity, in a case where the second electrode and the third electrode are formed by a pair of electrodes and are used to measure physical properties. In addition, as illustrated in FIGS. 2(a) and 2(b), regions surrounded by the exteriors of the electrodes on the front and rear surfaces of the piezoelectric plate 2a have approximately the same area, and are formed so that relative positions with the piezoelectric plate 2a interposed therebetween are approximately the same as each other. As mentioned above, in the piezoelectric device 1, the areas and the relative positions of the electrodes on the front and rear surfaces are the same as each other, respectively, and thus a signal obtained from thickness shear vibration of the piezoelectric plate 2a can be stabilized, thereby performing a measurement with good sensitivity. In addition, the second electrode 12 is connected to the switching portion 3 via the connection portion T2, and the third electrode 13 is connected to the switching portion 3 via the connection portion T3. Here, the first electrode 11, the second electrode 12, and the third electrode 13 are preferably made of a material which hardly changes in quality, such as gold, platinum, or carbon, but a material is not limited thereto as long as the material hardly changes in quality in usage circumstances. For example, the first electrode 11, the second electrode 12, and the third electrode may use indium tin oxide (ITO) depending on usage circumstances. In addition, the first electrode 11, the second electrode 12, and the third electrode 13 may be provided on the piezoelectric plate 2a with another material such as chrome or titanium interposed therebetween in order to improve adhesion with the piezoelectric plate 2a.

Figure 3:
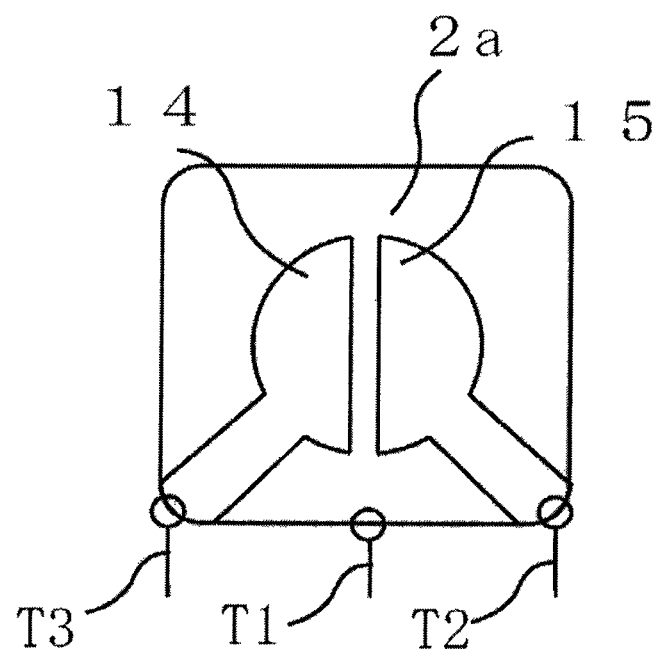
FIG. 3 is a schematic diagram illustrating another example of the rear surface of the piezoelectric plate of the first embodiment.

In addition, a configuration of the rear surface side of the piezoelectric plate 2a is not limited to the one illustrated in FIG. 2(b), and may be a configuration as illustrated in FIG. 3, for example.

FIG. 3 is a schematic diagram illustrating another configuration example of the rear surface side of the piezoelectric plate 2a. Here, in the piezoelectric plate 2a related to FIG. 3, the reference numeral 14 indicates a second electrode, and the reference numeral 15 indicates a third electrode. The second electrode 14 and the third electrode 15 are a pair of electrodes which are disposed so that at least parts thereof oppose each other. In other words, as illustrated in FIG. 3, the second electrode 14 and the third electrode 15 are not necessarily comb-shaped electrodes, and may be a pair of electrodes which have opposing parts in a state of being electrically insulated from each other (the second electrode 14 and the third electrode 15 may have any shape).

(Configuration of Switching Portion)

Next, a detailed configuration of the switching portion 3 will be described.

Figure 4:
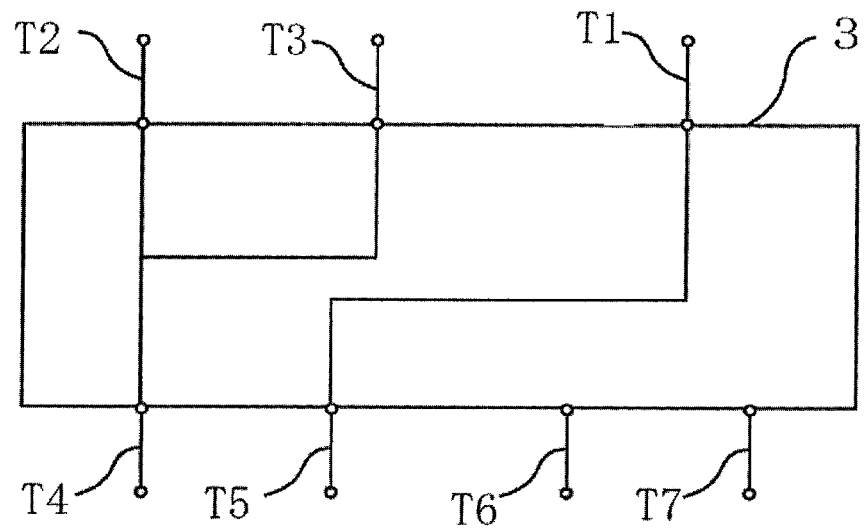
FIG. 4 is a diagram illustrating a switching portion of the first embodiment.
Figure 4:
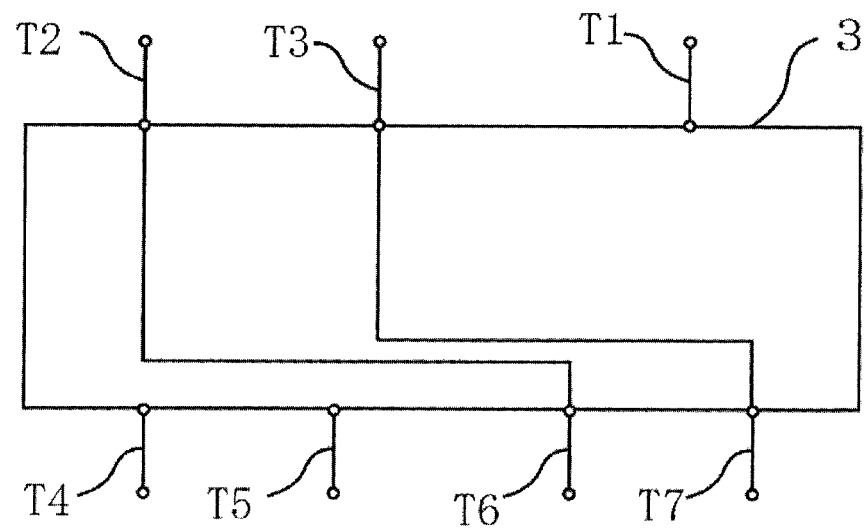

FIG. 4 is a diagram illustrating a configuration of the switching portion 3. The switching portion 3 has a function of switching a connection state between a state A (mass/viscoelasticity measurement mode) and a state B (electrical characteristic measurement mode).

Here, the state A is a connection state in which the connection portion T2 and the connection portion T3 are short-circuited so that the second electrode 12 and the third electrode 13 illustrated in FIG. 2 are equipotential, and thus a pseudo integrated electrode is formed. In other words, the switching portion 3 electrically short-circuits the second electrode 12 to the third electrode 13 so as to be equipotential, and thus can easily realize the state A. In addition, the state A is a state in which the switching portion 3 connects the integrated electrode to the connection portion T4, and the connection portion T1 is connected to the connection portion T5. The switching portion 3 forms a potential difference between the integrated electrode and the first electrode in this way. In other words, the first signal applying circuit 6 performs input and output of signals with the piezoelectric plate 2a via the connection portion T4 and the connection portion T5 in the state A, so as to cause thickness shear vibration in the piezoelectric plate 2a. In addition, the first signal detection circuit 5 may measure electrical characteristics such as admittance, conductance, susceptance, inductance, reactance, resistance, impedance, capacitance, and a resonance frequency of the piezoelectric plate 2a at that time. For this reason, the first signal detection circuit 5 illustrated in FIG. 1 may be used in a measurement device which acquires at least one output value (first output value) of these characteristics and measures at least one of physical quantities such as viscosity, elasticity, viscoelasticity, concentration, density, an amount of insoluble particles, a temperature, and mass of a liquid or a gas on the basis of the first output value, or a measurement device or a determination device using such physical quantities.

On the other hand, the state B is a state in which the connection portion T2 and the connection portion T3 are insulated from each other, the connection portion T2 is connected to the connection portion T6, and the connection portion T3 is connected to the connection portion T7. As mentioned above, the switching portion 3 switches a connection state to the state B so as to form a potential difference between the second electrode and the third electrode. In other words, the second signal applying circuit 9 exchanges signals between the connection portion T6 and the connection portion T7 in the state B, and thus the second signal detection circuit 8 can measure electrical characteristics such as impedance, admittance, conductance, susceptance, inductance, reactance, resistance, capacitance, electric conductivity, ionic conductivity, a dielectric constant, ion concentration, an oxidation-reduction potential, and oxidation-reduction substance concentration of a substance present between the second electrode 12 and the third electrode 13. For this reason, the second signal detection circuit 8 illustrated in FIG. 1 can acquire at least one output value (second output value) of these characteristics, and can measure a second physical quantity which is at least one of electric conductivity, ionic conductivity, a dielectric constant, ion concentration, an oxidation-reduction potential, and oxidation-reduction substance concentration on the basis of the second output value.

As mentioned above, the piezoelectric device 1 has a structure in which both of the second electrode 12 and the third electrode 13 as illustrated in FIG. 2 have two functions including a function of a single electrode and a function of a pair of electrodes formed by the second electrode and the third electrode as electrodes applying a signal to the piezoelectric element, and thus it is possible to acquire at least two pieces of physical property information without providing other measurement devices on the piezoelectric element. Therefore, the piezoelectric device 1 can implement a composite sensor which hardly influences thickness shear vibration.

In addition, the first circuit unit 7 of FIG. 1 includes the first signal applying circuit 6 which applies an input signal between the integrated electrode formed by the second electrode 12 and the third electrode 13, and the first electrode 11 in the state A of FIG. 4. In addition, the second circuit unit 10 of FIG. 1 includes the second signal applying circuit 9 which applies an input signal between the second electrode 12 and the third electrode 13 in the state B of FIG. 4. As mentioned above, since the piezoelectric device 1 is a piezoelectric device using the piezoelectric unit which has a structure in which both of the second electrode 12 and the third electrode 13 have two functions including a function of a single electrode and a function of a pair of electrodes formed by the second electrode and the third electrode as electrodes applying a signal to the piezoelectric element, it is possible to implement a composite sensor device which hardly influences thickness shear vibration when used to measure a physical property.

In addition, the first circuit unit 7 of FIG. 1 includes the first signal detection circuit 5 which detects an output signal based on a potential difference formed between the integrated electrode formed by the second electrode 12 and the third electrode 13, and the first electrode 11, in the state A of FIG. 4. Further, the second circuit unit 10 of FIG. 1 includes the second signal detection circuit 8 which detects an output signal based on a potential difference formed between the second electrode 12 and the third electrode 13 in the state B of FIG. 4. In addition, the first signal detection circuit 5 and the second signal detection circuit 8 are respectively used to measure a first physical quantity and a second physical quantity of a substance. As mentioned above, in the state A, the input signal applied between the integrated electrode formed by the second electrode 12 and the third electrode 13 and the first electrode 11 by the first signal applying circuit 6 included in the first circuit unit 7 causes thickness shear vibration reflecting a physical property of a substance which is in contact with the piezoelectric element in the piezoelectric element of the piezoelectric unit 4. In addition, the first signal detection circuit 5 measures the first physical quantity of the substance by measuring a thickness shear vibration state of the piezoelectric element. Further, in the state B of FIG. 4, the second electrode 12 and the third electrode 13 are made to input an electrical signal to a substance interposed therebetween by the second signal applying circuit 9 included in the second circuit unit 10 of FIG. 1. Furthermore, the second signal detection circuit 8 measures the second physical quantity of the substance by measuring an electrical signal which has passed through the substance. Moreover, in the piezoelectric device 1, if the signal detection circuit and the signal applying circuit are integrally formed in each of the first circuit unit 7 and the second circuit unit 10, it becomes easier to control phases of signals or to detect a phase difference thereof in both the inputting and outputting of the signals, and thus it is possible to implement a more accurate measurement device.

Figure 5:
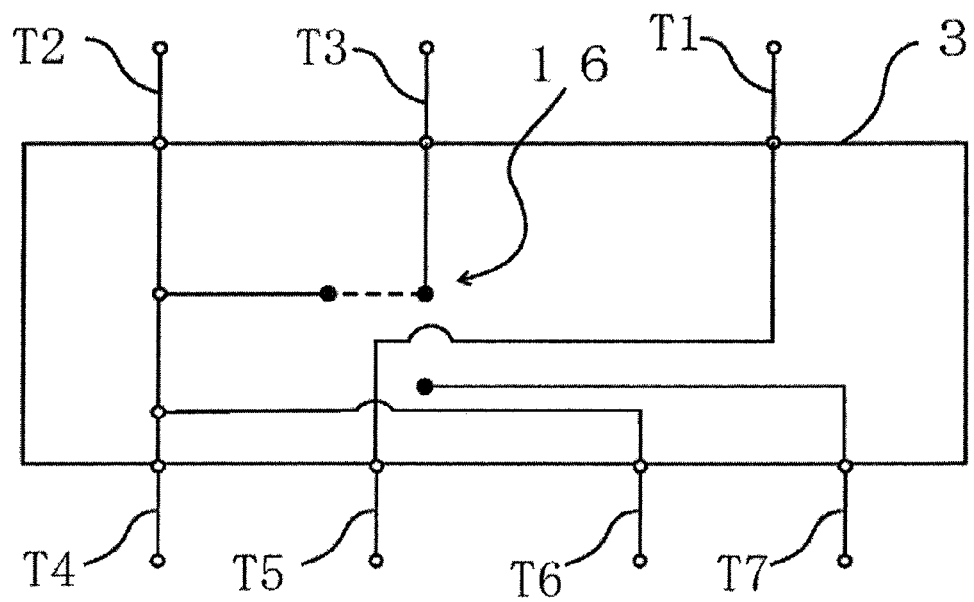
FIG. 5 is a diagram illustrating a switching portion using a switch in the first embodiment.
Figure 5:
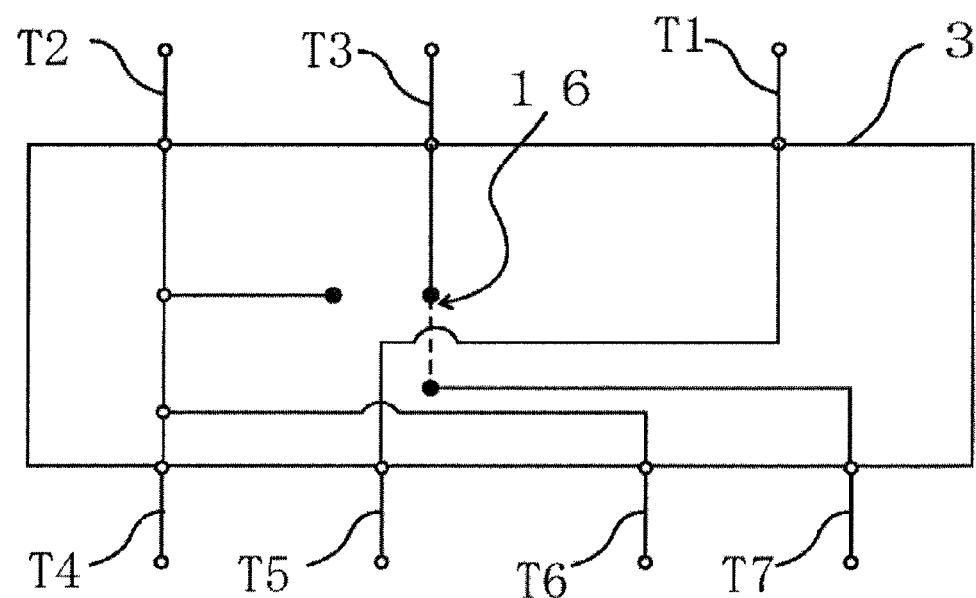

In addition, a configuration of the switching portion 3 is not limited to the one illustrated in FIG. 4, and may be a configuration illustrated in FIG. 5.

Here, FIG. 5 is a diagram illustrating the switching portion 3 using a switch 16. As illustrated in FIG. 5, switching between the state A and the state B may be performed by using the switch 16. In the state A, T2 and T4 are electrically connected to T3. In addition, in the state B, T3 is electrically connected to T7. Further, circuits of the switching portion 3 may be designed so that T2 is connected to T6 in the state A, and T2 is disconnected from T4 in the state B, by using a plurality of switches.

(Operation of Piezoelectric Device 1)

Next, an operation of the piezoelectric device 1 of the first embodiment will be described. First, a description will be made of an operation of the piezoelectric device 1 in the state A. A user immerses the piezoelectric vibrator 2 into a liquid sample so as to prepare for a measurement. Next, the user sets the switching portion 3 to the state A. Then, the first signal applying circuit 6 applies a voltage of any frequency between the connection portion T4 and the connection portion T5. In addition, the voltage is applied to the piezoelectric vibrator 2 via the switching portion 3 and the connection portions T1, T2 and T3. In the state A, the voltage is applied between the first electrode 11 and an integrated electrode formed by the second electrode 12 and the third electrode 13 on the piezoelectric plate 2a. Accordingly, the piezoelectric vibrator 2 causes thickness shear vibration so as to reflect a characteristic of the liquid sample. Then, the first signal detection circuit 5 acquires a first output value from the piezoelectric vibrator 2 which currently performs the thickness shear vibration.

Next, a description will be made of an operation of the piezoelectric device 1 in the state B. The user immerses the piezoelectric vibrator 2 into a liquid sample so as to prepare for a measurement. Next, the user sets the switching portion 3 to the state B. Then, the second signal applying circuit 9 applies a voltage between the connection portion T6 and the connection portion T7. A frequency of the applied voltage here will be described later in detail. In addition, the voltage is applied to the piezoelectric vibrator 2 via the switching portion 3 and the connection portions T2 and T3. In the state B, the voltage is applied between the second electrode 12 and the third electrode 13 on the piezoelectric plate 2a. Then, the second signal detection circuit 8 acquires a second output value which is an electrical characteristic reflecting a characteristic of the liquid sample.

Figure 17:
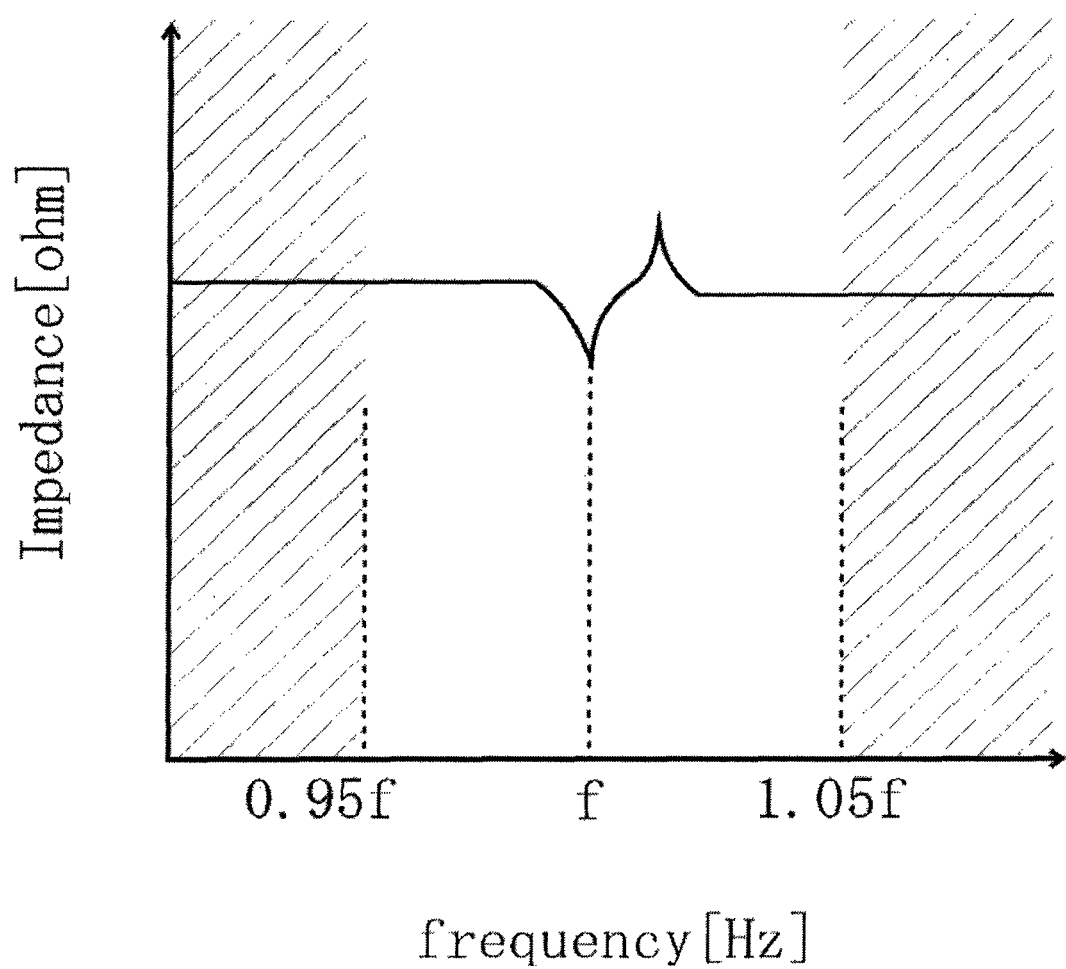
FIG. 17 is a diagram illustrating a frequency characteristic of a piezoelectric vibrator acquired by a first signal circuit in a state in which the piezoelectric vibrator of the first embodiment is immersed into a liquid sample.

Here, a frequency applied to the connection portions T6 and T7 will be described in detail with reference to FIG. 17. FIG. 17 is a diagram illustrating a frequency characteristic of the piezoelectric vibrator 2, acquired by the first signal detection circuit 5 in a state in which the piezoelectric vibrator 2 is immersed into the liquid sample. A resonance frequency of the piezoelectric vibrator 2 or a frequency of overtone vibration at this time is denoted by f. A frequency $f_{II}$ of a voltage applied between the connection portion T6 and the connection portion T7 by the second signal applying circuit 9 is preferably set in diagonal line regions excluding ±5% of frequency regions of f illustrated in FIG. 17 (that is, $f_{II}$ preferably satisfies a conditional expression of (Expression 1)). Accordingly, the piezoelectric device 1 can reduce noise of the second output value which is obtained by the second signal detection circuit 8, and thus can perform a measurement with higher accuracy.

[Expression 2]

$$(f_n > 1.05 \times nf) \cap (f_n < 0.95 \times nf), n=1,3,5,$$ (Expression 2)

[Second Embodiment]

Next, a second embodiment of the piezoelectric device 1 will be described with reference to FIG. 6. The piezoelectric device 1 according to the present embodiment is substantially the same as that of the first embodiment except that the first circuit unit 7 is different from that of the first embodiment. In addition, in the following, among constituent elements of the piezoelectric device 1, the same constituent elements as in the above-described first embodiment are given the same reference numeral, and description thereof will be omitted.

Figure 6:
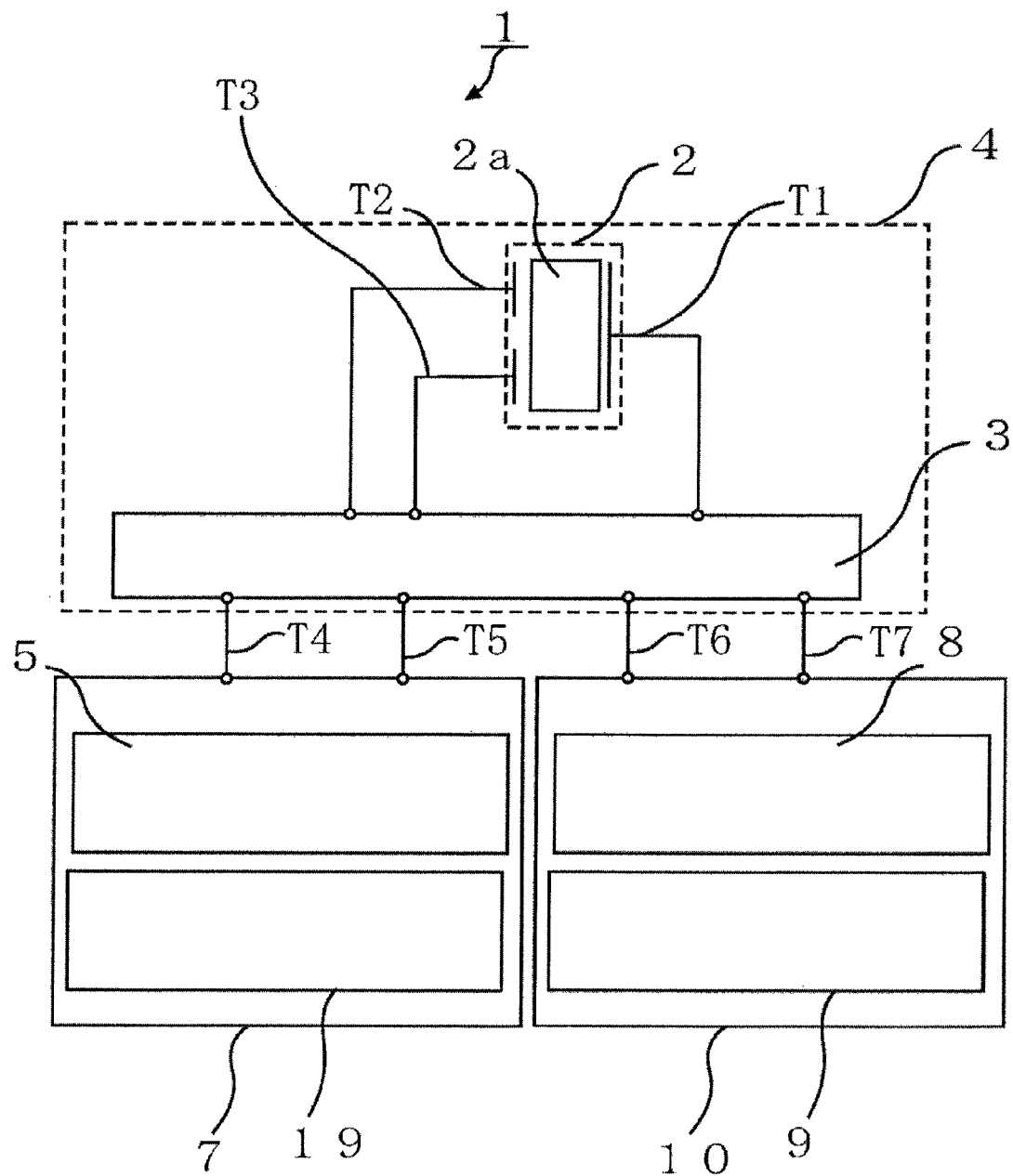
FIG. 6 is a configuration diagram illustrating a piezoelectric device of a second embodiment.

FIG. 6 is a configuration diagram illustrating the piezoelectric device 1 of the present embodiment. The piezoelectric device 1 of the present embodiment includes a piezoelectric unit 4, a first circuit unit 7 connected to the piezoelectric unit 4, and a second circuit unit 10 connected to the piezoelectric unit 4. In addition, the first circuit unit 7 is constituted by a first signal detection circuit 5 and an oscillation circuit 19.

As mentioned above, in the piezoelectric device 1 according to the present embodiment, the first signal applying circuit of the first embodiment is replaced with the oscillation circuit 19 which causes oscillation at a resonance frequency in a fundamental mode or harmonic vibration of the piezoelectric element, and thus it is possible to make the piezoelectric element easily oscillate.

(Operation of Piezoelectric Device 1)

Next, an operation of the piezoelectric device 1 of the second embodiment will be described. First, a description will be made of an operation in the state A. A user immerses the piezoelectric vibrator 2 into a liquid sample so as to prepare for a measurement. Next, the user sets the switching portion 3 to the state A. Then, the oscillation circuit 19 applies a voltage of any frequency between the connection portion T4 and the connection portion T5. In addition, the voltage is applied to the piezoelectric vibrator 2 via the switching portion 3 and the connection portions T1, T2 and T3. In the state A, the voltage is applied between the first electrode 11 and an integrated electrode formed by the second electrode 12 and the third electrode 13 on the piezoelectric plate 2a. Accordingly, the piezoelectric vibrator 2 causes thickness shear vibration so as to reflect a characteristic of the liquid sample. Then, the first signal detection circuit 5 acquires a first output value from the piezoelectric vibrator 2 which currently performs the thickness shear vibration.

In addition, an operation in the state B is the same as that in the first embodiment.

[Third Embodiment]

Next, a description will be made of a third embodiment of the piezoelectric device 1 with reference to FIGS. 7 and 8. The piezoelectric device 1 according to the present embodiment is substantially the same as that of the first embodiment except that configurations of a switching portion 24 and a circuit unit connected to the switching portion 24 are different from those of the first embodiment. In addition, in the following, among constituent elements of the piezoelectric device 1, the same constituent elements as in the above-described first embodiment are given the same reference numeral, and description thereof will be omitted.

Figure 7:
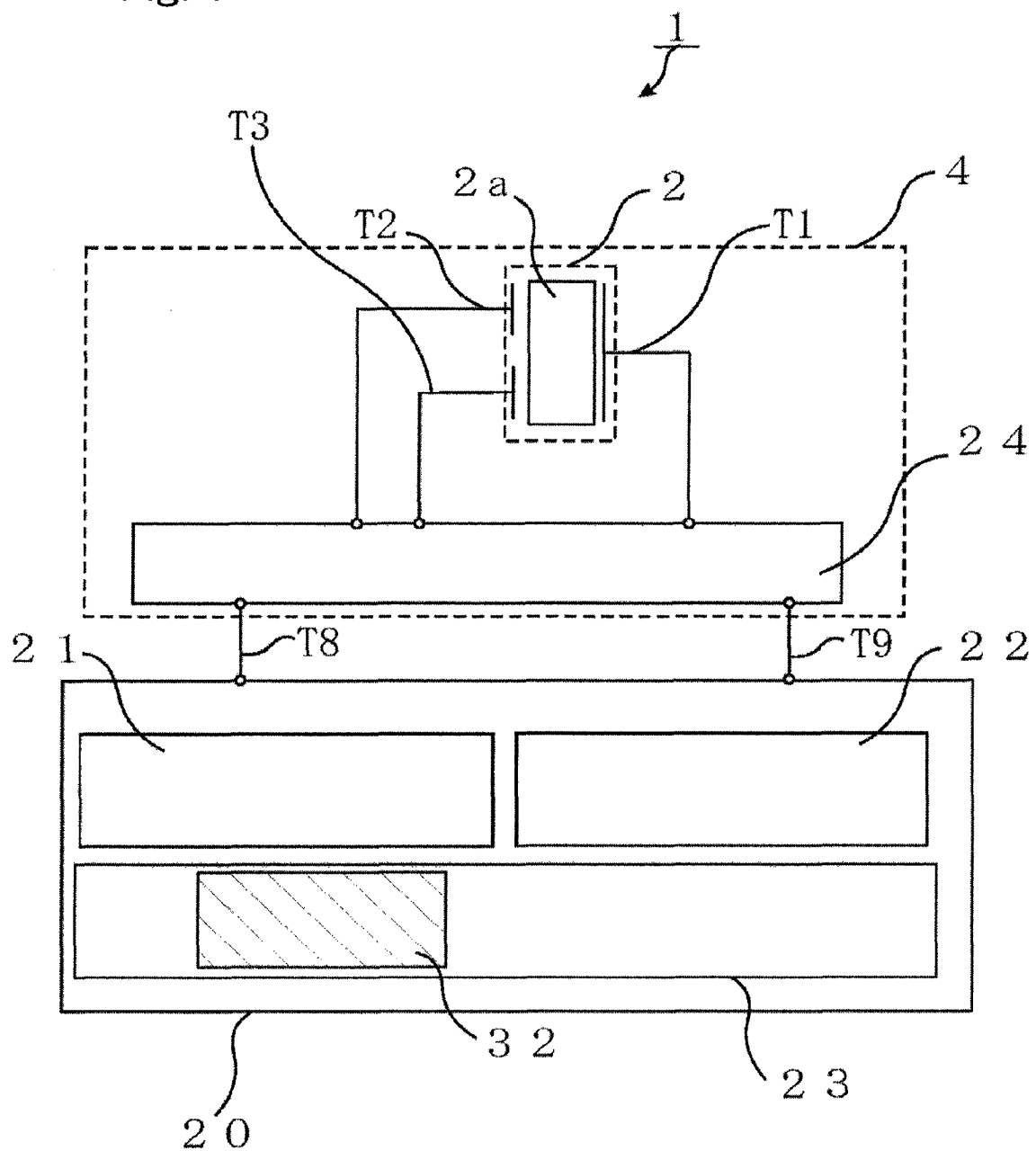
FIG. 7 is a configuration diagram illustrating a piezoelectric device of a third embodiment.

FIG. 7 is a configuration diagram illustrating the piezoelectric device 1 of the third embodiment. The piezoelectric device 1 of the present embodiment includes a piezoelectric unit 4 and a common circuit unit 20. The piezoelectric unit 4 includes a piezoelectric vibrator 2, and connection portions T1, T2 and T3 which are the same as the constituent elements described in the first embodiment, and the switching portion 24 connected to the piezoelectric vibrator 2 via the connection portions T1, T2 and T3.

As mentioned above, in the piezoelectric device 1 according to the present embodiment, the first circuit unit and the second circuit unit according to the first embodiment are replaced with the common circuit unit 20 which is an identical common unit. In other words, the first circuit unit and the second circuit unit are made common, and thus the piezoelectric device 1 can be miniaturized. Here, the common circuit unit 20 is constituted by a first signal detection circuit 21, a second signal detection circuit 22, and a common signal applying circuit 23. In addition, the common signal applying circuit 23 is provided with an oscillator circuit 32. In other words, the signal applying circuits provided in the respective circuit units in the first embodiment are made common by the common signal applying circuit 23, and thus a configuration of the piezoelectric device 1 is simplified. Further, the circuit unit 20 is connected to the switching portion 24 via connection portions T8 and T9.

Figure 8:
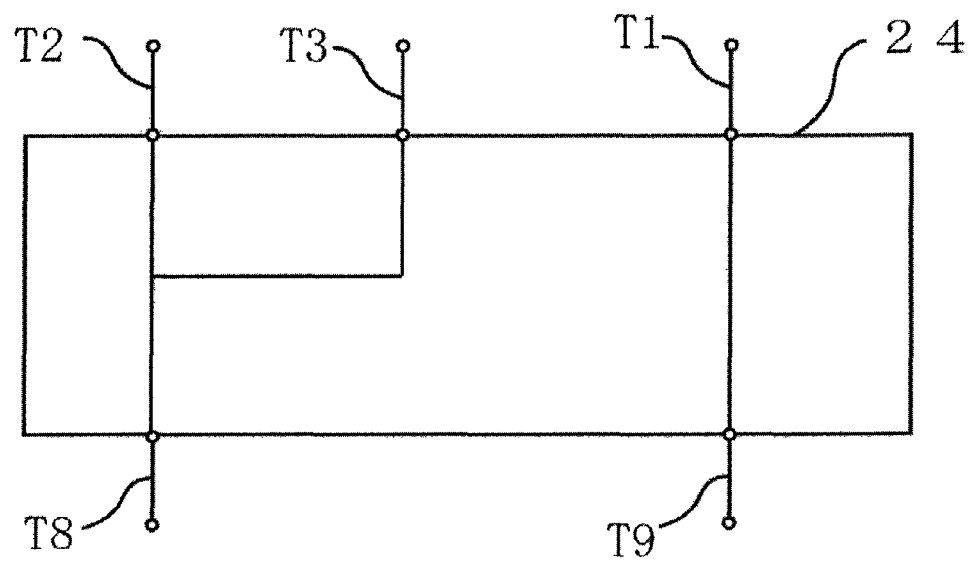
FIG. 8 is a diagram illustrating a switching portion of the third embodiment.
Figure 8:
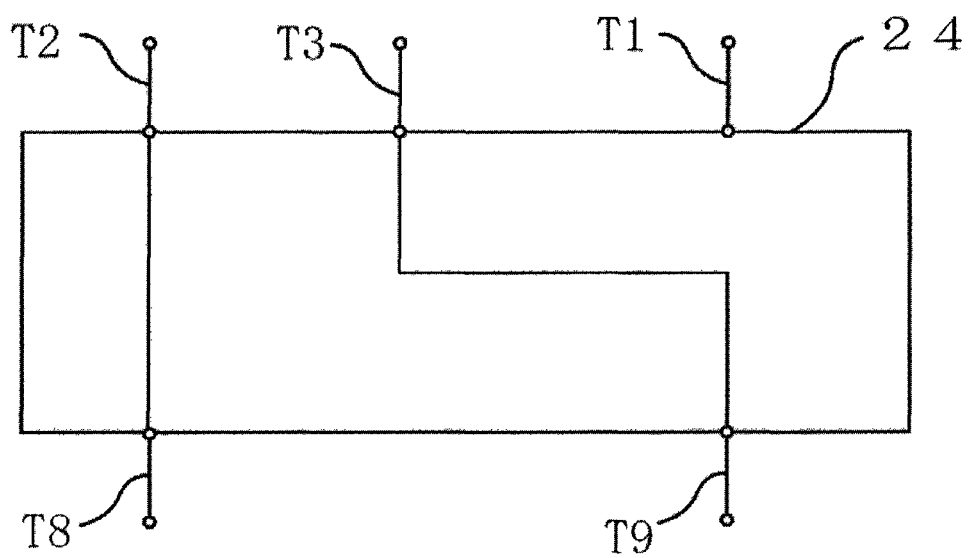

FIG. 8 is a diagram illustrating a configuration of the switching portion 24 of the third embodiment. The switching portion 24 of the present embodiment has a function of switching a connection state between a state A2 (mass/viscoelasticity measurement mode) and a state B2 (electrical characteristic measurement mode). Here, the state A2 is a state in which the connection portion T2 and the connection portion T3 are short-circuited and are connected to the connection portion T8, and the connection portion T1 is connected to the connection portion T9. On the other hand, the state B2 is a state in which the connection portion T2, the connection portion T3, and the connection portion T1 are insulated from each other, the connection portion T2 is connected to the connection portion T8, and the connection portion T3 is connected to the connection portion T9.

Here, although not illustrated, the common signal applying circuit 23 illustrated in FIG. 7 is used as both an applying circuit which applies a signal between the second electrode 12 and the third electrode 13, and an applying circuit which applies a signal to both surfaces of the piezoelectric vibrator 2 by applying the signal to a combination of the first electrode 11 and the second electrode 12 or the first electrode 11 and the third electrode 13. In addition, the common signal applying circuit 23 applies a signal between the second electrode 12 and the third electrode 13 by electrically connecting the connection portions T2 and T3 to each other when the switching portion 24 is set to the state A2. Further, the common signal applying circuit 23 operates as an applying circuit which applies a signal to both sides of the piezoelectric vibrator 2 when the switching portion 24 is set to the state B2.

(Operation of Piezoelectric Device 1)

Next, an operation of the piezoelectric device 1 of the third embodiment will be described. First, a description will be made of an operation of the piezoelectric device 1 in the state A2. To begin with, a user immerses the piezoelectric vibrator 2 into a liquid sample so as to prepare for a measurement. Next, the user sets the switching portion 24 to the state A2. Then, the common signal applying circuit 23 applies a voltage of any frequency between the connection portion T8 and the connection portion T9. In addition, the voltage is applied to the piezoelectric vibrator 2 via the switching portion 24 and the connection portions T1, T2 and T3. In the state A2, the voltage is applied between the first electrode 11 and an integrated electrode formed by the second electrode 12 and the third electrode 13 on the piezoelectric plate 2a. Accordingly, the piezoelectric vibrator 2 causes thickness shear vibration so as to reflect a characteristic of the liquid sample. Then, the first signal detection circuit 21 acquires a first output value from the piezoelectric vibrator 2 which currently performs the thickness shear vibration.

Next, a description will be made of an operation of the piezoelectric device 1 in the state B2. First, the user immerses the piezoelectric vibrator 2 into a liquid sample so as to prepare for a measurement. Next, the user sets the switching portion 24 to the state B2. Then, the common signal applying circuit 23 applies a voltage of any frequency between the connection portion T8 and the connection portion T9. In addition, the voltage is applied to the piezoelectric vibrator 2 via the switching portion 24 and the connection portions T2 and T3. In the state B2, the voltage is applied between the second electrode 12 and the third electrode 13 on the piezoelectric plate 2a. Then, the second signal detection circuit 22 acquires a second output value which is an electrical characteristic reflecting a characteristic of the liquid sample.

[Fourth Embodiment]

Next, a fourth embodiment of the piezoelectric device 1 will be described with reference to FIG. 9. The piezoelectric device 1 according to the present embodiment is substantially the same as that of the first embodiment except that a configuration of a circuit unit is different from that of the third embodiment. In addition, in the following, among constituent elements of the piezoelectric device 1, the same constituent elements as in the above-described third embodiment are given the same reference numeral, and description thereof will be omitted.

Figure 9:
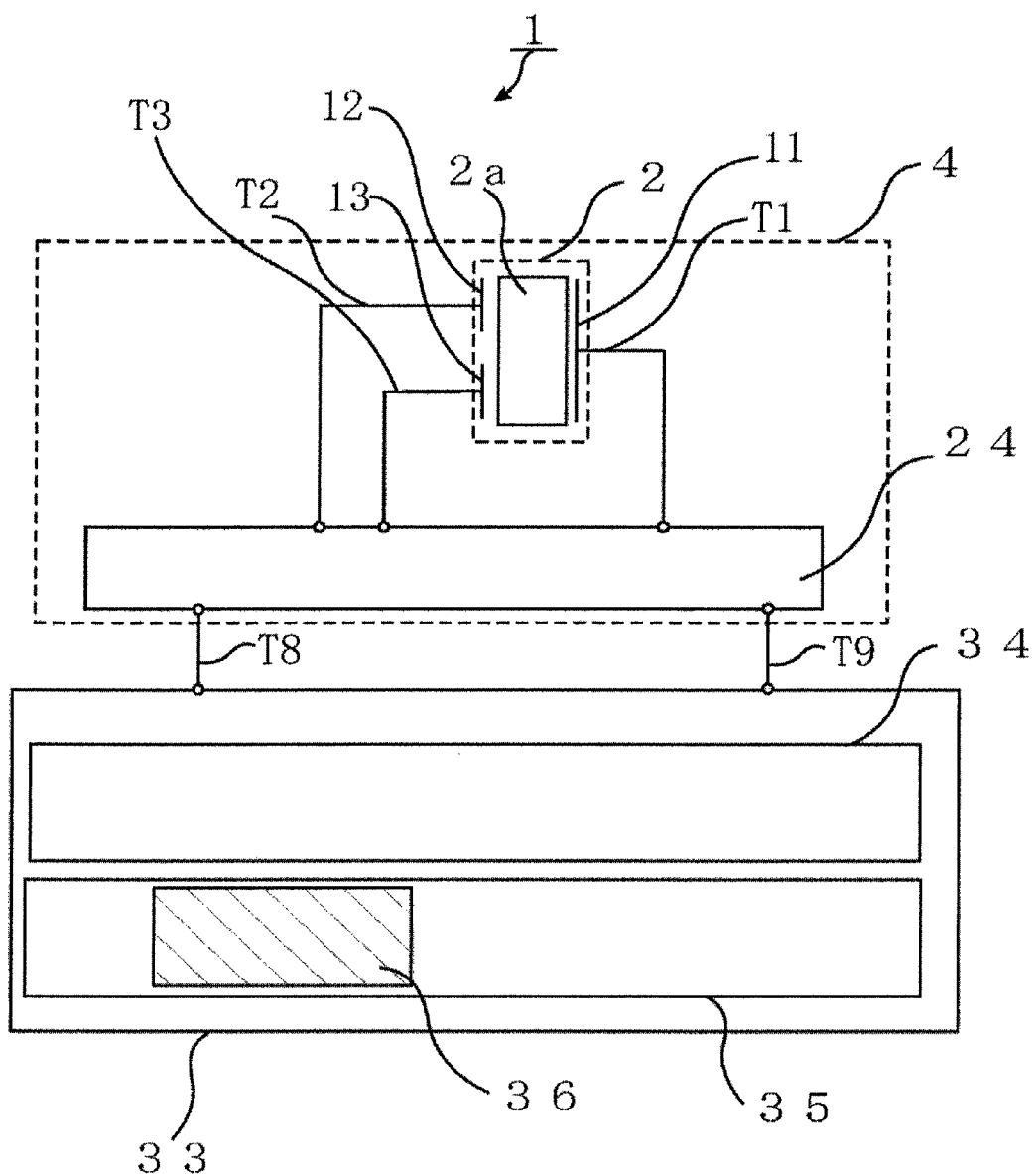
FIG. 9 is a diagram illustrating a switching portion of a fourth embodiment.

FIG. 9 is a configuration diagram illustrating the piezoelectric device 1 of the present embodiment. The piezoelectric device 1 of the present embodiment includes a piezoelectric unit 4 and a common circuit unit 33. The piezoelectric unit 4 includes a piezoelectric vibrator 2, and connection portions T1, T2 and T3 which are the same as the constituent elements described in the third embodiment, and the switching portion 24 connected to the piezoelectric vibrator 2 via the connection portions T1, T2 and T3. The common circuit unit 33 is constituted by a common signal detection circuit 34 and a common signal applying circuit 35. In addition, the common signal applying circuit 35 is provided with an oscillator circuit 36. Further, the common circuit unit 33 is connected to the switching portion 24 via the connection portions T8 and T9.

As mentioned above, each of the signal applying circuit and the signal detection circuit in the common circuit unit 33 is formed as a single circuit, and thus the piezoelectric device 1 is simplified.

(Operation of Piezoelectric Device 1)

Next, an operation of the piezoelectric device 1 of the fourth embodiment will be described. First, a description will be made of an operation of the piezoelectric device 1 in the state A2. To begin with, a user immerses the piezoelectric vibrator 2 into a liquid sample so as to prepare for a measurement. Next, the user sets the switching portion 24 to the state A2. Then, the common signal applying circuit 35 applies a voltage of any frequency between the connection portion T8 and the connection portion T9. In addition, the voltage is applied to the piezoelectric vibrator 2 via the switching portion 24 and the connection portions T1, T2 and T3. In the state A2, the voltage is applied between the first electrode 11 and an integrated electrode formed by the second electrode 12 and the third electrode 13 on the piezoelectric plate 2a. Accordingly, the piezoelectric vibrator 2 causes thickness shear vibration so as to reflect a characteristic of the liquid sample. Then, the common signal detection circuit 34 acquires a first output value from the piezoelectric vibrator 2 which currently performs the thickness shear vibration.

Next, a description will be made of an operation of the piezoelectric device 1 in the state B2. First, the user immerses the piezoelectric vibrator 2 into a liquid sample so as to prepare for a measurement. Next, the user sets the switching portion 24 to the state B2. Then, the common signal applying circuit 35 applies a voltage of any frequency between the connection portion T8 and the connection portion T9. In addition, the voltage is applied to the piezoelectric vibrator 2 via the switching portion 24 and the connection portions T2 and T3. In the state B2, the voltage is applied between the second electrode 12 and the third electrode 13 on the piezoelectric plate 2a. Then, the common signal detection circuit 34 acquires a second output value which is an electrical characteristic reflecting a characteristic of the liquid sample.

[Fifth Embodiment]

Next, a fifth embodiment of the piezoelectric device 1 will be described with reference to FIGS. 10 and 11. The piezoelectric device 1 according to the present embodiment is substantially the same as that of the first embodiment except that the piezoelectric vibrator 2 is different from that of the first embodiment. In addition, in the following, among constituent elements of the piezoelectric device 1, the same constituent elements as in the above-described first embodiment are given the same reference numeral, and description thereof will be omitted.

Figure 10:
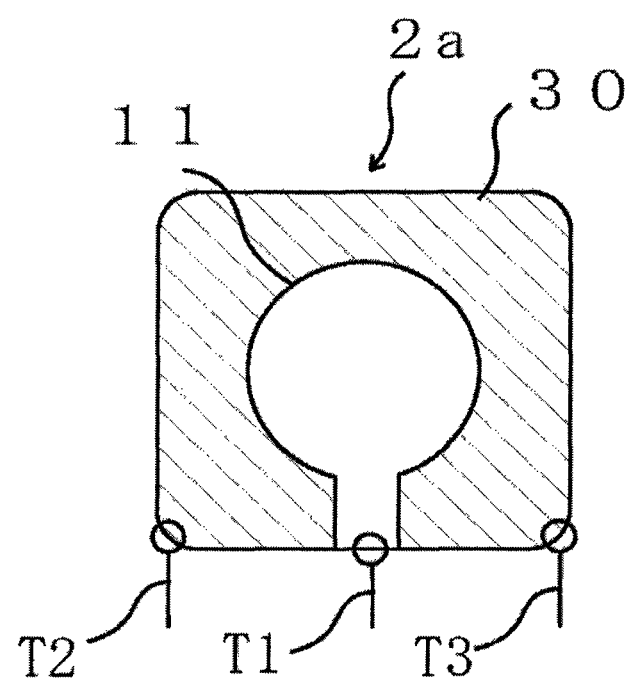
FIG. 10 is a diagram illustrating a front surface of a piezoelectric plate of a fifth embodiment.

FIG. 10 is a diagram illustrating a front surface of the piezoelectric plate 2a of the fifth embodiment. The piezoelectric plate 2a of the present embodiment includes a sensitive film 30 provided on its front surface. As the sensitive film 30, an appropriate film is used so as to match its application. For example, a specific substance in a liquid or a gas which is a measurement sample is selectively attached to the sensitive film 30, and thus a thickness shear vibration state of the piezoelectric plate 2a varies. In other words, the piezoelectric device 1 can measure mass, density, and concentration in the liquid or the gas in relation to the attached substance on the basis of the variation. In addition, in a case where a measurement sample is used for depositing an insoluble component through a chemical reaction, the piezoelectric device 1 can measure an amount of deposited insoluble particles. Here, as the sensitive film 30, an appropriate one is preferably selected and used depending on a substance which is a measurement target, such as an oxide semiconductor, an organic polymer sensitive film, and a biomaterial containing sensitive film using an antigen-antibody reaction or the like. Further, if a material whose viscoelasticity greatly varies due to attachment of a slight amount of substances thereto is used, the sensitive film 30 may be used to amplify a variation in a thickness shear vibration state of the quartz crystal plate 2.

Accordingly, the piezoelectric device 1 can improve measurement sensitivity in a measurement using thickness shear vibration.

Figure 11:
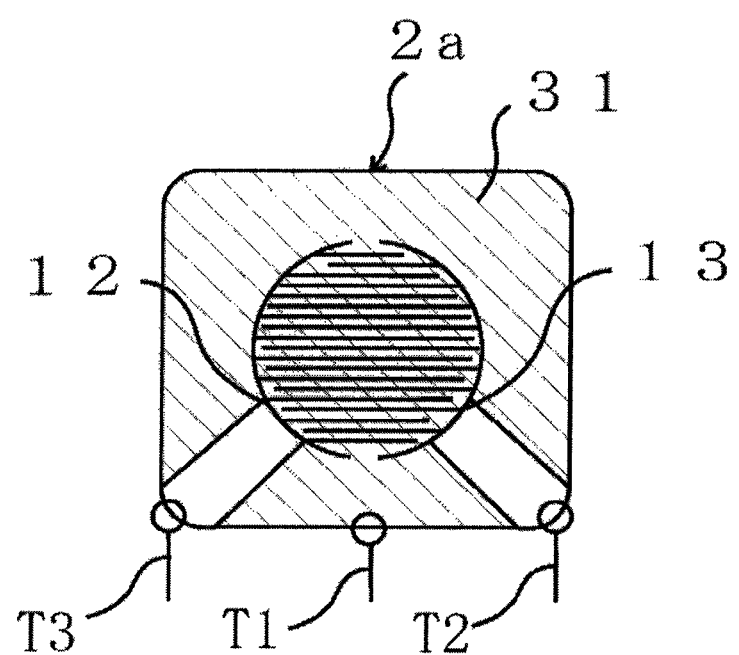
FIG. 11 is a diagram illustrating a rear surface of the piezoelectric plate of the fifth embodiment.

FIG. 11 is a diagram illustrating a rear surface of the piezoelectric plate 2a. In the piezoelectric plate 2a of FIG. 10, an example has been described in which a sensitive film 31 is formed only on the front surface, but a sensitive film may be formed only on the rear surface as illustrated in FIG. 11. Alternatively, in the piezoelectric plate 2a, sensitive films may be formed on both the front surface and the rear surface.

[Sixth Embodiment]

Next, a sixth embodiment of a piezoelectric determination apparatus 26 will be described with reference to FIGS. 12 and 13. The piezoelectric determination apparatus 26 according to the present embodiment includes a piezoelectric device 1 which has substantially the same configuration as that in the first embodiment. In addition, the piezoelectric device 1 is not limited to one having the same configuration as in the first embodiment, and may use any piezoelectric device of the above-described first to fifth embodiments. Further, in the following description, among constituent elements of the piezoelectric device 1, the same constituent elements as in the above-described first embodiment are given the same reference numeral, and description thereof will be omitted.

Figure 12:
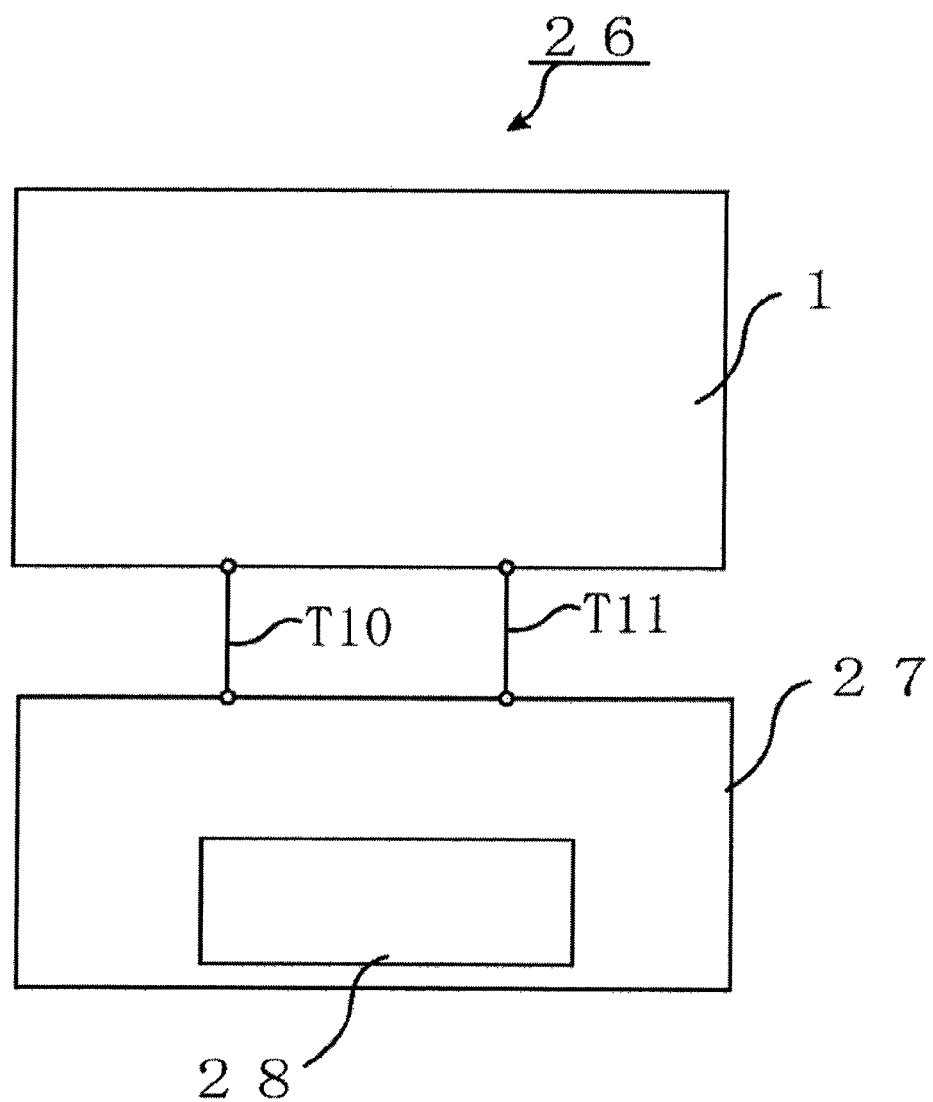
FIG. 12 is a configuration diagram illustrating an embodiment of a piezoelectric determination apparatus according to the present invention.

FIG. 12 is a configuration diagram illustrating a configuration of the piezoelectric determination apparatus 26 according to the present embodiment. The piezoelectric determination apparatus 26 includes the piezoelectric device 1 having the same configuration as the one described in the first embodiment, and a determination device 27 which is connected to the first signal detection circuit 5 and the second signal detection circuit 8 of the piezoelectric device 1 (refer to FIG. 1) via connection portions T10 and T11. The determination device 27 determines a state of a substance by using a first physical quantity and a second physical quantity obtained from the piezoelectric device 1.

As mentioned above, since the piezoelectric determination apparatus 26 uses the piezoelectric unit having a structure in which both of the second electrode and the third electrode have two functions including a function of a single electrode and a function of a pair of electrodes formed by the second electrode and the third electrode as electrodes applying a signal to the piezoelectric element, it is possible to implement the determination apparatus by using a composite sensor which hardly influences thickness shear vibration.

In addition, the determination device 27 is provided with a display portion 28, and thus can display a determination result performed by the determination device 27, a physical quantity measured by the piezoelectric device 1, a resonance frequency or an equal circuit constant of the piezoelectric vibrator 2, a setting condition of the piezoelectric determination apparatus 26, or the like on the display portion 28. In other words, the determination device 27 is provided with the display portion 28, and thus a user can easily confirm a determination result.

Figure 13:
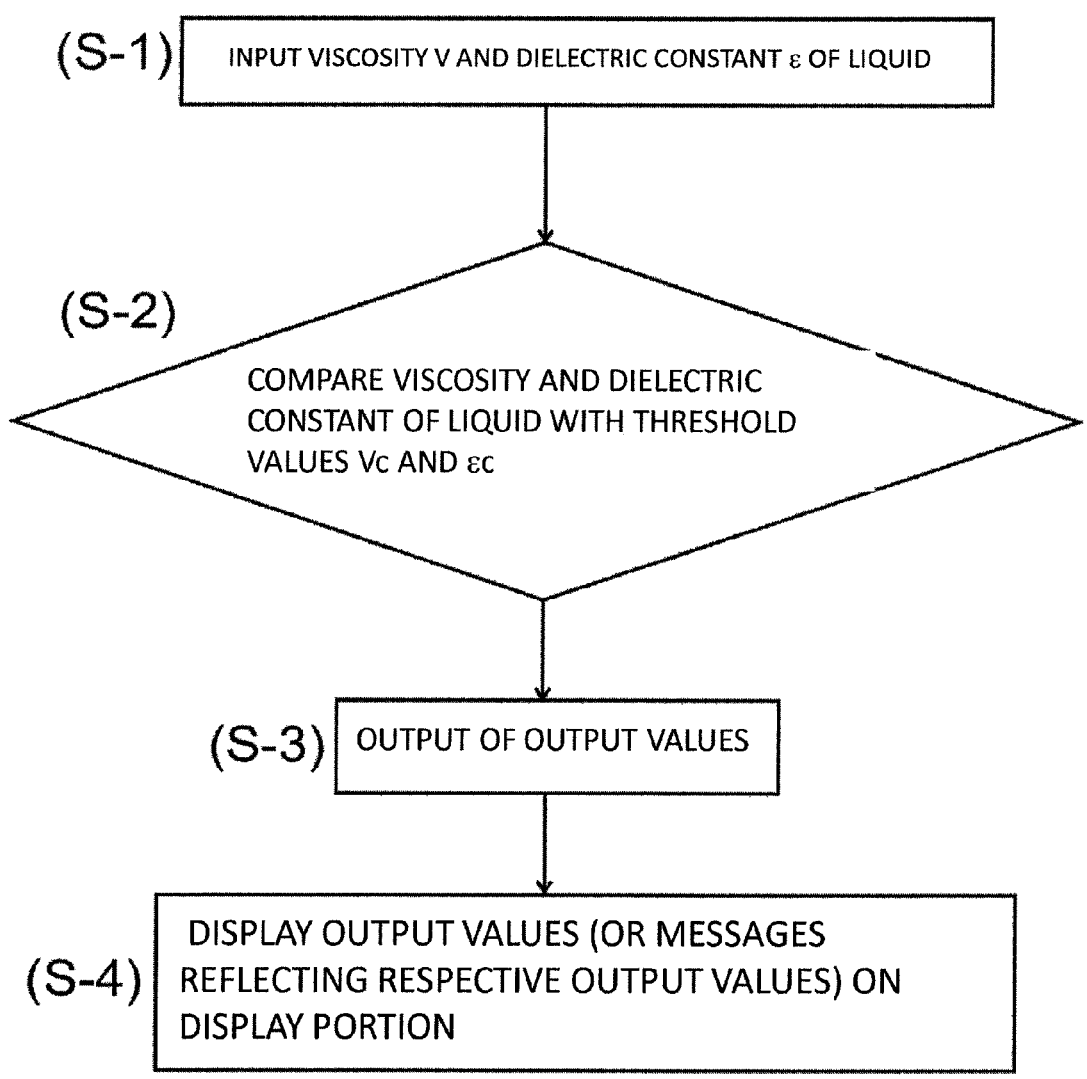
FIG. 13 is a flowchart illustrating a process of deriving a determination result by using a determination device.

FIG. 13 is a flowchart illustrating a process in which the determination device 27 of the piezoelectric determination apparatus 26 illustrated in FIG. 12 derives a determination result. First, two physical quantities including viscosity V and a dielectric constant $\in$ of a substance are input to the determination device 27 by the piezoelectric device 1 (S-1). Here, the viscosity V is the first physical quantity obtained from a resonance frequency which is the first output value. In addition, the dielectric constant $\in$ is the second physical quantity obtained from impedance which is the second output value. However, the viscosity V or the dielectric constant $\in$ can be obtained from other output values, and thus an output value for obtaining each physical quantity is not limited thereto. Next, the determination device 27 compares the viscosity V with a preset viscosity threshold value Vc, and, similarly, compares the dielectric constant c with a preset impedance threshold value $\in$c (S-2). Then, the determination device 27 outputs an output value which reflects a comparison result in (S-2) to the display portion 28 (S-3). Finally, the display portion 28 displays the output value or a message reflecting the output value (S-4).

As mentioned above, the piezoelectric determination apparatus 26 measures the first physical quantity and the second physical quantity obtained from the piezoelectric device 1, and determines a state of a substance by using both of the first physical quantity and the second physical quantity. In other words, the piezoelectric determination apparatus 26 determines characteristics or states of a substance by using the piezoelectric unit which has a structure in which both of the second electrode 12 and the third electrode 13 have two functions including a function of a single electrode and a function of a pair of electrodes formed by the second electrode 12 and the third electrode 13 as electrodes applying a signal to the piezoelectric element. As a result, the piezoelectric determination apparatus 26 can determine characteristics, states, or the like of a substance on the basis of two or more characteristics of the substance, and thus can derive a determination result with higher reliability.

Here, a description will be made of a case where deterioration of a fatty oil is determined by the piezoelectric determination apparatus 26 as a specific example of determination. In addition, it is assumed that, in relation to the fatty oil, it is determined that a characteristic thereof deteriorates when an upper limit of the viscosity threshold value Vc and a lower limit of the dielectric constant threshold value cc are exceeded. The determination device 27 outputs 1 if V/Vc≥1 or ∈/∈c≤1, and 0 if otherwise as output values. Further, the determination device 27 sends a signal to the display portion 28 so that "determination result: deterioration" is displayed when an output value of 1 is obtained, and "determination result: normal" is displayed when an output value of 0 is obtained. In this way, the piezoelectric determination apparatus 26 is implemented which can determine that the fatty oil deteriorates in a case where both or either of the viscosity and the dielectric constant characteristics of the fatty oil exceeds a threshold value which is a criterion.

[Seventh Embodiment]

Next, a seventh embodiment of the piezoelectric device will be described with reference to FIG. 16. The piezoelectric device 1 according to the present embodiment is substantially the same as that of the first embodiment except that a configuration of a switching portion 40 is different from that of the first embodiment. In addition, in the following, among constituent elements of the piezoelectric device 1, the same constituent elements as in the above-described first embodiment are given the same reference numeral, and description thereof will be omitted.

Figure 16:
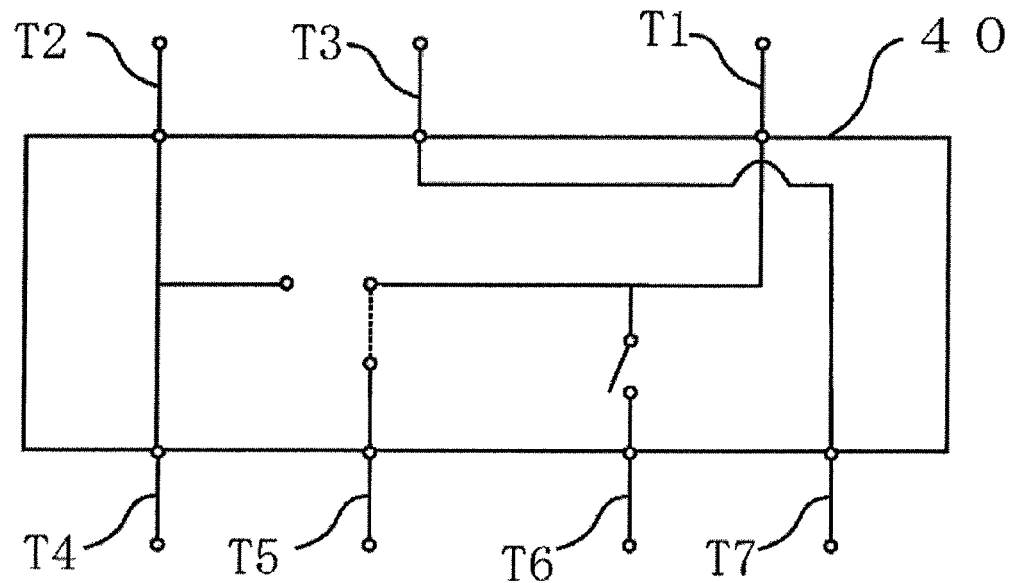
FIG. 16 is a diagram illustrating a switching portion of a seventh embodiment.
Figure 16:
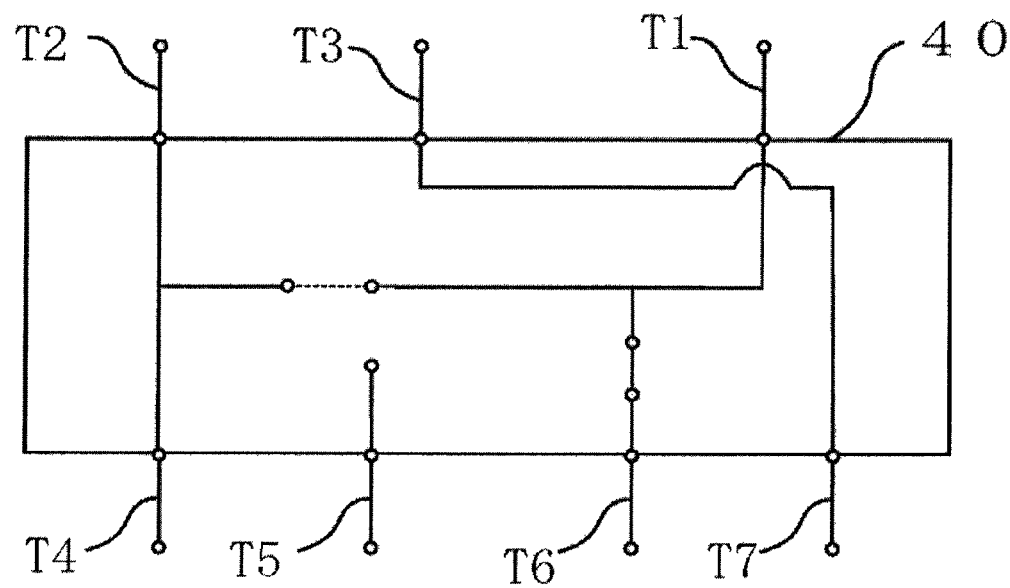

FIG. 16 is a diagram illustrating a configuration of the switching portion 40 of the seventh embodiment. The switching portion 40 of the present embodiment has a function of switching a connection state between a state A3 and a state B3. The state A3 is a state in which the connection portion T2 is connected to the connection portion T4, and the connection portion T1 is connected to the connection portion T5. In other words, the switching portion 40 forms a connection state in which a potential difference occurs between the second electrode 12 which is one electrode of comb-shaped electrodes and the first electrode 11 so that the piezoelectric vibrator 2 causes thickness shear vibration. Here, one of the comb-shaped electrodes is not necessarily required to be the second electrode 12, and a state in which the third electrode 13 is connected in the same manner may be the state A3. On the other hand, the state B3 is a state in which the connection portion T2 and the connection portion T1 are short-circuited and are connected to the connection portion T6, and the connection portion T3 is connected to the connection portion T7.

As mentioned above, the piezoelectric device 1 short-circuits the second electrode 12 which is one of the comb-shaped electrodes to the first electrode 11 on the front surface, and thus it is possible to reduce regulation method of a measurement system. For this reason, the piezoelectric device 1 can stably acquire the second output value obtained between the comb-shaped electrodes, and thus it is possible to perform a measurement using the piezoelectric device 1 with high accuracy.

[Eighth Embodiment]

Next, an eighth embodiment of the piezoelectric determination apparatus 26 will be described with reference to FIG. 18. The piezoelectric determination apparatus 26 according to the present embodiment is substantially the same as that of the sixth embodiment except that configurations of a piezoelectric device 43 and a determination device 29 are different from those of the sixth embodiment. In addition, in the following, among constituent elements of the piezoelectric determination apparatus 26, the same constituent elements as in the above-described sixth embodiment are given the same reference numeral, and description thereof will be omitted.

Figure 18:
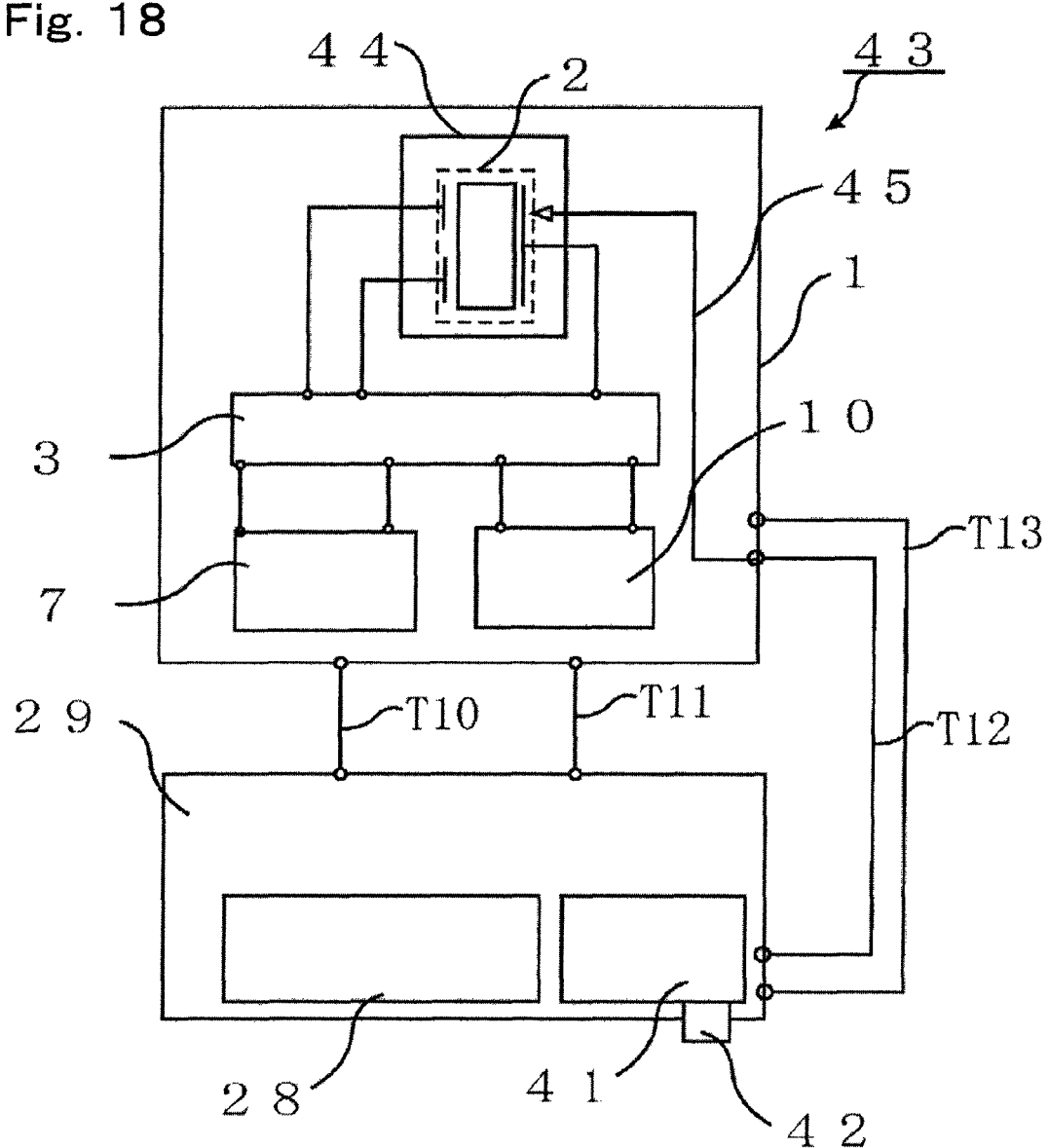
FIG. 18 is a diagram illustrating a piezoelectric determination apparatus of an eighth embodiment.

FIG. 18 is a configuration diagram illustrating an embodiment of the piezoelectric determination apparatus 26 according to the present invention. The determination device 29 of the present embodiment includes a temperature management portion 41 which can measure and control a temperature of a substance. The temperature management portion 41 is electrically connected to the determination device 29 and the display portion 28 in the determination device 29. In addition, the temperature management portion 41 is provided with an adjuster 42 which can adjust a temperature of a substance from outside.

Further, the piezoelectric device 43 of the present embodiment includes a temperature control mechanism 44 which can accommodate both a substance serving as a measurement sample of the piezoelectric vibrator 2 and a temperature measurement terminal 45 for measuring a temperature of the substance, and can control a temperature of the internal substance on the basis of an electrical signal from an external device. Here, the temperature control mechanism 44 is electrically connected to the piezoelectric device 43, and the piezoelectric device 43 is connected to the temperature management portion 41 via connection portions T12 and T13 through the determination device 29.

An electrical signal for a temperature of a substance which is measured by the temperature measurement terminal 45 is input to the temperature management portion 41 via the connection portion T12. A temperature value output from the temperature management portion 41 is displayed on the display portion 28. Therefore, a user can confirm the temperature of the substance from the outside by using the display portion 28. Meanwhile, an electrical signal for a set temperature which is externally input by the adjuster 42 is input to the temperature control mechanism 44 via the connection portion T13.

As mentioned above, the piezoelectric determination apparatus 26 can determine a state of a substance under the same temperature condition by measuring the first physical quantity or the second physical quantity of the substance while controlling a temperature of the substance. For this reason, the piezoelectric determination apparatus 26 can perform determination of a state more accurately even if a substrate or a piezoelectric vibrator which is highly dependent on a temperature is used.

[Measurement Examples of Measuring Two Physical Quantities of Liquid Samples]

For reference, a description will be made of measurement examples in which two physical quantities of liquid samples have been actually measured.

As fatty oil samples for measurement, a fatty oil A, a fatty oil B, and a fatty oil C were prepared, and a resonance frequency variation using a QCM measurement, which is an equivalent value to the integrated electrode and the first electrode 11, and a capacitance variation using the comb-shaped electrodes, which is an equivalent value to the second electrode 12 and the third electrode 13, were measured for each fatty oil when a heating process was repeatedly performed every eight hours at 200° C.

Hereinafter, respective descriptions will be made of a relationship between oxidative deterioration of the fatty oils and a result of the QCM measurement and a relationship between the oxidative deterioration of the fatty oils and a result of measuring electrical characteristics by using the comb-shaped electrodes.

Figure 14:
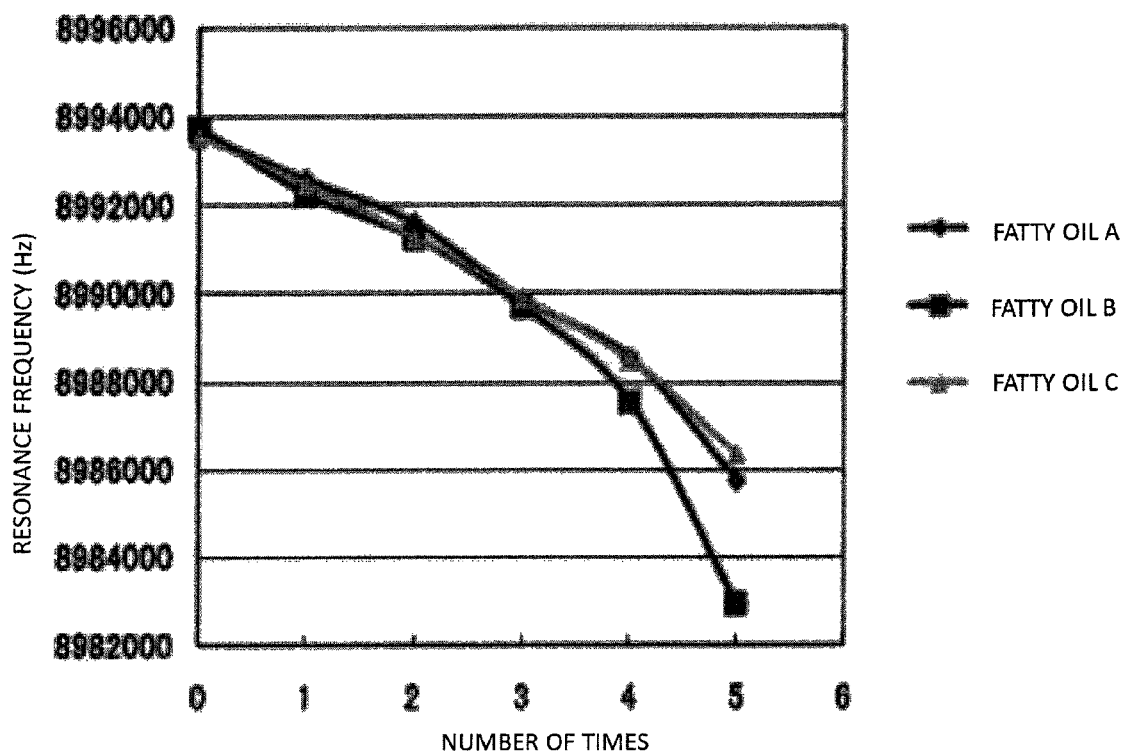
FIG. 14 is a graph illustrating a resonance frequency measurement result of a fatty oil sample, obtained by using a QCM measurement.

FIG. 14 is a graph illustrating a resonance frequency measurement result of the QCM measurement using a quartz crystal vibrator.

The transverse axis expresses the number of heating processes of the fatty oil samples, and the longitudinal axis expresses a resonance frequency [Hz]. It can be seen from this graph that the resonance frequency decreases as the heating process is performed for a longer time in all of the fatty oil samples including the fatty oil A, the fatty oil B, and the fatty oil C. Generally, it is known that, if viscosity of a liquid increases, a resonance frequency decreases. At this time, it can be estimated that oxidative deterioration of the fatty oils occurs by repeatedly performing the heating process, and, as a result, it can be said that a reduction in the resonance frequency, that is, an increase in the viscosity occurs.

Figure 15:
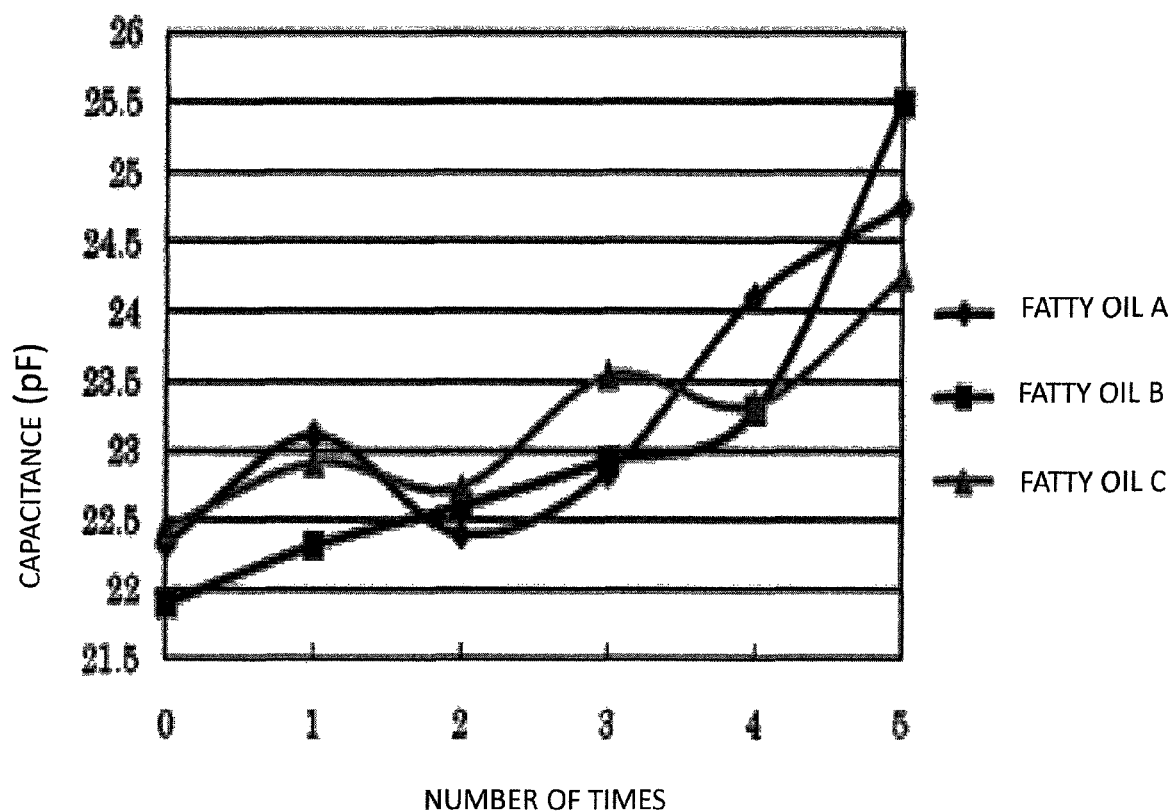
FIG. 15 is a graph illustrating a capacitance measurement result of a fatty oil sample, obtained by using a comb-shaped electrode.

FIG. 15 is a graph illustrating a result of a capacitance measurement using the comb-shaped electrodes.

The transverse axis expresses the number of heating processes of the fatty oil samples, and the longitudinal axis expresses capacitance [pF]. It can be seen from this graph that, although the measurement data fluctuates, the capacitance tends to gradually increase in all of the fatty oils including the fatty oil A, the fatty oil B, and the fatty oil C. Since the capacitance reflects a dielectric constant of a substance, it can be estimated that dielectric constants of the fatty oils vary in oxidative deterioration due to the repetition of the heating process.

From the above description, it is possible to obtain a plurality of physical property values by measuring electrical characteristics of a substance using a pair of electrodes, formed by the comb-shaped electrodes or the like in addition to electrical characteristics of the piezoelectric vibrator such as a quartz crystal vibrator. Accordingly, it can be seen that, even in a case where one of the physical property values cannot be acquired as stable data for a certain reason like in this instance, a determination of a substance is performed by using data which is more stably measured, and thus it is possible to determine a substance state with high reliability. In addition, this is also effective in a case where a determination reference is set by using intersections of a plurality of data items, or the like.

Particularly, it is more preferable that a substance be a liquid, and deterioration in characteristics of the liquid be measured. A deterioration state of the liquid is determined by using the piezoelectric unit which has a structure in which both of the second electrode and the third electrode have two functions including a function of a single electrode and a function of a pair of electrodes formed by the second electrode and the third electrode as electrodes applying a signal to the piezoelectric element, and thus the deterioration state of the liquid can be determined on the basis of two or more characteristics of the liquid. Therefore, it is possible to perform determination of deterioration of a liquid with higher reliability.

REFERENCE SIGNS LIST 1, 43: Piezoelectric device
2: Piezoelectric vibrator
2a: Piezoelectric plate
3, 24, 40: Switching portion
4: Piezoelectric unit
5, 21: First signal detection circuit
6: First signal applying circuit
7: First circuit unit
8, 22: Second signal detection circuit
9: Second signal applying circuit
10: Second circuit unit
11: First electrode
12, 14: Second electrode
13, 15: Third electrode
16: Switch
17, 18, 32, 36: Oscillator circuit
19: Oscillation circuit
20, 33: Common circuit unit
23, 35: Common signal applying circuit
34: Common signal detection circuit
26: Piezoelectric determination apparatus
27, 29: Determination device
28: Display portion
41: Temperature management portion
42: Adjuster
44: Temperature control mechanism
45: Temperature measurement terminal
30, 31: Sensitive film
T1 to T13: Connection portion

The invention claimed is:

1. A piezoelectric unit comprising:
a piezoelectric element that causes thickness shear vibration;
an electrode portion that includes a first electrode provided on one surface of the piezoelectric element, and a second electrode and a third electrode which are provided on an opposite surface to the one surface of the piezoelectric element and are electrically insulated from each other; and
a switching portion that is connected to the first electrode, the second electrode, and the third electrode, and switches a connection state of each electrode,
wherein the switching portion can switch a measurement mode between a mass/viscoelasticity measurement mode which is a connection state of the electrodes for measuring mass of a substance which is in contact with the piezoelectric element or viscoelasticity of a peripheral environment by causing the thickness shear vibration of the piezoelectric element, and an electrical characteristic measurement mode which is a connection state of the electrodes for measuring electrical characteristics between the second electrode and the third electrode.

2. The piezoelectric unit according to claim 1, wherein the piezoelectric element is a quartz crystal vibrator.

3. The piezoelectric unit according to claim 1, wherein the second electrode and the third electrode have a comb shape.

4. The piezoelectric unit according to any one of claim 1, wherein the mass/viscoelasticity measurement mode is a connection state in which the second electrode and the third electrode are maintained in an equal potential so that a pseudo integrated electrode is formed, and a potential difference is formed between the integrated electrode and the first electrode.

5. The piezoelectric unit according to any one of claim 1, wherein the mass/viscoelasticity measurement mode is a connection state in which a potential difference is formed between the first electrode and one of the second electrode and the third electrode.

6. The piezoelectric unit according to any one of claim 1, wherein the electrical characteristic measurement mode is a connection state in which a potential difference is formed between the second electrode and the third electrode in a state in which the first electrode is short-circuited to one of the second electrode and the third electrode.

7. The piezoelectric unit according to claim 1, wherein a region surrounded by an exterior of the first electrode has the same area as an area of a region surrounded by a combined exterior of the second electrode and the third electrode, and relative positions of the electrodes on front and rear surfaces with the piezoelectric element interposed therebetween match each other.

8. The piezoelectric unit according to claim 1, wherein the piezoelectric element is provided with a sensitive film on the front surface.

9. A piezoelectric device comprising:
the piezoelectric unit according to claim 1;
a first circuit unit that is connected to the piezoelectric unit; and
a second circuit unit that is connected to the piezoelectric unit,
wherein the first circuit unit includes a first signal applying circuit that applies a first input signal to the electrode portion in a connection state of the mass/viscoelasticity measurement mode, and
wherein the second circuit unit includes a second signal applying circuit that applies a second input signal to the electrode portion in a connection state of the electrical characteristic measurement mode.

10. The piezoelectric device according to claim 9, wherein the first circuit unit includes a first signal detection circuit that detects a first output signal responding to the first input signal which is applied by the first signal applying circuit, and can measure a first physical quantity based on the first output signal, and
wherein the second circuit unit includes a second signal detection circuit that detects a second output signal responding to the second input signal which is applied by the second signal applying circuit, and can measure a second physical quantity based on the second output signal.

11. The piezoelectric device according to claim 10, wherein the first signal applying circuit includes an oscillator circuit that can set any frequency of an applied signal.

12. The piezoelectric device according to claim 10, wherein the first signal applying circuit is an oscillation circuit which causes oscillation at a resonance frequency in a fundamental mode or harmonic vibration of the piezoelectric element.

13. The piezoelectric device according to claim 10, wherein the second signal applying circuit includes an oscillator circuit that can set any frequency of an applied signal.

14. The piezoelectric device according to claim 10, wherein a frequency $f_{II}$ of an input signal which is input by the second signal applying circuit in a state in which the piezoelectric element is in contact with a substance having the first physical quantity or the second physical quantity satisfies (Expression 1) which is a conditional expression using a resonance frequency f which is acquired on the basis of the first output signal detected by the first signal detection circuit in a state of being in contact with the substance.

[Expression 3]

$$(f_{II} > 1.05 \times nf) \cap (f_{II} < 0.95 \times nf), n = 1, 3, 5,$$ (Expression 3)

15. The piezoelectric device according to claim 10, wherein the first signal detection circuit acquires, as a first output value, any one of admittance, conductance, susceptance, inductance, reactance, resistance, impedance, capacitance, and a resonance frequency during shear vibration of the piezoelectric element on the basis of the detected first output signal.

16. The piezoelectric device according to claim 10, wherein the first physical quantity is at least one of viscosity, elasticity, viscoelasticity, concentration, density, an amount of insoluble particles, a temperature, and mass based on the first output value.

17. The piezoelectric device according to 10, wherein the second signal detection circuit acquires, as a second output value, anyone of current, a potential difference, impedance, admittance, conductance, susceptance, inductance, reactance, resistance, and capacitance on the basis of the detected second output signal.

18. The piezoelectric device according to claim 10, wherein the second physical quantity is at least one of electric conductivity, ionic conductivity, a dielectric constant, ion concentration, an oxidation-reduction potential, and oxidation-reduction substance concentration based on the second output value.

19. A piezoelectric determination apparatus comprising:
the piezoelectric device according to claim 10; and
a determination device that is connected to the first signal detection circuit and the second signal detection circuit,
wherein the determination device determines characteristics or states of the substance by using the first physical quantity and the second physical quantity.

20. The piezoelectric determination apparatus according to claim 19, wherein the determination device includes a display portion that displays a result of determination performed by the determination device.

21. The piezoelectric determination apparatus according to claim 19, wherein the determination device further includes a temperature management portion that measures a temperature of the substance.

22. The piezoelectric determination apparatus according to claim 21, wherein the temperature management portion includes a temperature control section that controls a temperature of the substance.

23. A state determination method of determining a state of a substance by using the piezoelectric determination apparatus according to claim 19, the method comprising:
measuring the first physical quantity and the second physical quantity; and
determining a state of the substance by using both of the first physical quantity and the second physical quantity.

24. The state determination method according to claim 23, wherein the substance is a liquid, and
wherein the state is a deterioration state of characteristics of the liquid.

25. The piezoelectric device according to claim 9, wherein the first circuit unit and the second circuit unit are formed by an identical common unit.

26. The piezoelectric device according to claim 25, wherein the first signal applying circuit and the second signal applying circuit are formed by an identical common signal applying circuit, and
wherein the common signal applying circuit includes an oscillator circuit that can set any frequency.

27. The piezoelectric device according to claim 25, wherein the first signal detection circuit and the second signal detection circuit are formed by an identical common signal detection circuit.

28. The piezoelectric unit according to claim 1, wherein the second and third electrodes are provided on the same surface of the piezoelectric element corresponding to the opposite surface thereof; wherein the electrode portion is configured so that the substance is interposed between the second and third electrodes; and wherein the electrical characteristic measurement mode is a connection state of the electrode portion for measuring an electrical characteristic of the substance interposed between the second and third electrodes.

29. A piezoelectric device comprising:
a piezoelectric element configured to undergo thickness-shear vibration;
an electrode portion comprised of a first electrode provided to one side of the piezoelectric element, and a second electrode and a third electrode electrically insulated from each other and provided to the reverse side of the piezoelectric element from the side to which the first electrode is provided;
a mass/viscoelasticity measurement circuit, coupled to the first electrode and to one of the second electrode and the third electrode, for measuring a mass or viscoelasticity of a substance in contact with the piezoelectric element by exciting the piezoelectric element;
an electrical characteristic measurement circuit, coupled to the second electrode and the third electrode, for measuring electrical characteristics between the second electrode and the third electrode;
a switching unit that switches between the mass/viscoelasticity measurement circuit and the electrical characteristic measurement circuit;
wherein the second and third electrodes are provided on the same surface of the piezoelectric element corresponding to the reverse side thereof;
wherein the electrode portion is configured so that the substance is interposed between the second and third electrodes; and
wherein the electrical characteristic measurement circuit is configured to measure an electrical characteristic of the substance interposed between the second and third electrodes.

* * * * *